US012564452B2

(12) United States Patent (10) Patent No.: US 12,564,452 B2
Comi et al. (45) Date of Patent: Mar. 3, 2026

(54) SYSTEMS AND METHODS FOR SURGICAL TRACKING AND PREDICTION

(71) Applicant: Ulysses Medical Technologies, Inc., New York, NY (US)

(72) Inventors: Francesca Comi, Merate (IT); Antonio Tomarchio, New York, NY (US); Walter Ferrara, Milan (IT); William Nespoli, Jersey City, NJ (US)

(73) Assignee: Ulysses Medical Technologies, Inc., New York, NY (US)

( * ) Notice: Subject to any disclaimer, the term of this patent is extended or adjusted under 35 U.S.C. 154(b) by 326 days.

(21) Appl. No.: 18/295,136

(22) Filed: Apr. 3, 2023

(65) Prior Publication Data

US 2023/0310095 A1 Oct. 5, 2023

Related U.S. Application Data

(60) Provisional application No. 63/378,200, filed on Oct. 3, 2022, provisional application No. 63/366,948, filed (Continued)

(51) Int. Cl.
A61B 34/20 (2016.01)
G16H 30/40 (2018.01)
A61M 25/01 (2006.01)

(52) U.S. Cl.
CPC ............. *A61B 34/20* (2016.02); *G16H 30/40* (2018.01); *A61B 2034/2048* (2016.02); *A61B 2034/2051* (2016.02); *A61M 2025/0166* (2013.01)

(58) Field of Classification Search
CPC ............ A61B 34/20; A61B 2034/2048; A61B 2034/2051; G16H 30/40; A61M 2025/0166
See application file for complete search history.

(56) References Cited

U.S. PATENT DOCUMENTS 7,278,991 B2 * 10/2007 Morris ............... A61B 18/1477
606/41
8,239,001 B2 * 8/2012 Verard ................... A61B 90/39
600/407

(Continued)

FOREIGN PATENT DOCUMENTS

JP 2022-513805 A 2/2022
KR 10-2017-0006582 A 1/2017

(Continued)

OTHER PUBLICATIONS

International Search Report and Written Opinion dated Aug. 7, 2023 in Application No. PCT/US2023/017346 in 8 pages.

*Primary Examiner* — Julian W Woo
(74) *Attorney, Agent, or Firm* — Knobbe Martens Olson & Bear LLP

(57) ABSTRACT

A system may include a first sensor element comprising an accelerometer. A system may include a first communications interface. A system may include a second sensor package comprising. A system may include a second sensor element comprising an accelerometer. A system may include a second communications interface, wherein the first sensor package is configured to be disposed in a reference position, wherein the second sensor package is configured to move relative to the first sensor package, wherein the first communications interface is configured to enable electronic communications with at least one of the second sensor package or a computer system, wherein the second communications interface is configured to enable electronic communications with at least one of the first sensor package or the computer system.

15 Claims, 20 Drawing Sheets

Related U.S. Application Data on Jun. 24, 2022, provisional application No. 63/362,
447, filed on Apr. 4, 2022.

(56)                  References Cited

U.S. PATENT DOCUMENTS

| | | | | |
|---|---|---|---|---|
| 8,369,921 | B2 * | 2/2013 | Tegg .................. | A61N 1/36542 |
| | | | | 600/373 |
| 9,387,048 | B2 * | 7/2016 | Donhowe .............. | A61B 34/20 |
| 11,058,494 | B2 | 7/2021 | Bueno et al. | |
| 2022/0167922 | A1 | 6/2022 | Gross | |
| 2025/0126147 | A1 * | 4/2025 | Koral .................. | H04L 63/1416 |

FOREIGN PATENT DOCUMENTS

| | | | |
|---|---|---|---|
| WO | WO 2012-109760 | A1 | 8/2012 |
| WO | WO 2014-009893 | A1 | 1/2014 |

* cited by examiner

802

802

1100

1100

SYSTEMS AND METHODS FOR SURGICAL TRACKING AND PREDICTION

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57. This application claims the benefit of U.S. Provisional Application No. 63/362,447, filed Apr. 4, 2022, U.S. Provisional Application No. 63/366,948, filed Jun. 24, 2022, and U.S. Provisional Application No. 63/378,200, filed Oct. 3, 2022, the contents of each of which are hereby incorporated by reference in their entirety.

BACKGROUND

Field

This disclosure relates to tracking of surgical movements. Some embodiments relate to systems and methods for predicting movements for performing a procedure on a patient. Some embodiments relate to improving surgical procedures. Description of Related Art The approaches described in this section are approaches that could be pursued, but not necessarily approaches that have been previously conceived or pursued. Thus, unless otherwise indicated, it should not be assumed that any of the material described in this section qualifies as prior art merely by virtue of its inclusion in this section.

Tracking movements during surgery can be important for a wide variety of reasons. For example, surgeons have a need to know where instruments, implants, and so forth are inside the patient, especially for non-invasive procedures that use catheters, endoscopes, and the like, where manipulations performed by the physician may not translate directly into movements of the medical instrument inside the patient's body.

SUMMARY

While tracking the movements performed by surgical staff and the positioning and movement of surgical instruments inside a patient are important, there is currently limited ability to track movement. For example, fluoroscopy is commonly used to monitor catheter insertion and manipulation, the placement of devices such as stents, and during orthopedic surgery to aid in joint replacements. However, fluoroscopy is limited because it only provides a 2D image. Additional views can be obtained, but require the movement of the fluoroscopy equipment, which may be cumbersome and time-consuming, and may also pose problems for surgeons and other operating room staff who must be mindful of working near an active radiation source.

A tracking system can preferably track the motion of a surgical instrument in real-time and in three dimensions, which may be used to provide real-time guidance to a surgeon during a procedure. The movements may also be recorded so that the physician can review after surgery. In some embodiments, the movement information may be used in combination with other information such as patient outcomes, patient demographic information, and patient test results to determine movements that lead to better or worse patient outcomes, which can be used in planning future surgical procedures.

In some aspects, the techniques described herein relate to a system for monitoring motion during a surgical procedure including: a first sensor package including: a first sensor element including an accelerometer; and a first communications interface; a second sensor package including: a second sensor element including an accelerometer; and a second communications interface; wherein the first sensor package is configured to be disposed in a reference position, wherein the second sensor package is configured to move relative to the first sensor package, wherein the first communications interface is configured to enable electronic communications with at least one of the second sensor package or a computer system, wherein the second communications interface is configured to enable electronic communications with at least one of the first sensor package or the computer system.

In some aspects, the techniques described herein relate to a system, wherein the first sensor element includes a first microelectromechanical system, wherein the second sensor element includes a second microelectromechanical system.

In some aspects, the techniques described herein relate to a system, wherein the first sensor package includes a first patch including: the first communications interface; the first sensor element; an enclosure having a bottom surface and surrounding the first communications interface and the first sensor element; and an adhesive disposed on the bottom surface of the enclosure and configured to affix the enclosure to a surgical instrument.

In some aspects, the techniques described herein relate to a system, wherein the first sensor package is disposed near a distal end 4, wherein the pigtail includes an outlet port disposed near the distal end of the pigtail, the outlet port configured to enable delivery of a contrast agent into the body of the patient, In some aspects, the techniques described herein relate to a system, wherein the second sensor package further includes: a power source, the power source configured to provide electrical power to the first sensor element and the first communications interface.

In some aspects, the techniques described herein relate to a system, wherein the power source includes a non-rechargeable battery.

In some aspects, the techniques described herein relate to a system, wherein the power source includes a rechargeable battery.

In some aspects, the techniques described herein relate to a system, wherein the second sensor package further includes inductive charging circuitry, the inductive charging circuitry configured to recharge the rechargeable battery.

In some aspects, the techniques described herein relate to a system, wherein the second sensor package is sterilizable.

In some aspects, the techniques described herein relate to a system, wherein the second sensor element includes a sensor capsule, the sensor capsule further including: a flexible substrate; a rigid sleeve; and a flexible wrap including a biocompatible material, wherein the second sensor element and the second communications interface are disposed on a top surface of the flexible substrate, wherein the rigid sleeve is fitted on top of a top surface of the second sensor element and the second communications interface, wherein the flexible wrap is disposed on an outer surface of the rigid sleeve, wherein the sensor capsule, when in an assembled state, has an approximately cylindrical shape, wherein the sensor capsule, when in an assembled state, includes an opening in a middle of the sensor capsule, the opening configured to enable the sensor capsule to be fitted to a catheter.

In some aspects, the techniques described herein relate to a system, wherein an outer diameter of the sensor capsule is from about 2 mm to about 10 mm.

In some aspects, the techniques described herein relate to a system, wherein the second sensor element further includes an electrostatic sensor, the system further including: a sheath configured to receive a catheter, the sheath including: a plurality of electrodes, the plurality of electrodes distributed along a length of the sheath.

In some aspects, the techniques described herein relate to a system, wherein a distance between neighboring electrodes of the plurality of electrodes is constant.

In some aspects, the techniques described herein relate to a system, wherein each electrode of the plurality of electrodes is configured to be a connected to a potential source.

In some aspects, the techniques described herein relate to a system, wherein the second sensor package includes one or more of a pressure sensor, a temperature sensor, or a pH sensor.

In some aspects, the techniques described herein relate to a system, further including: a sheath; and a plurality of sheath sensor elements disposed along a length of the sheath.

In some aspects, the techniques described herein relate to a system, wherein the second communications interface is configured to electronically communicate using one or more of Zigbee, Bluetooth, Bluetooth Low Energy, Near Field Communications, or Wi-Fi.

In some aspects, the techniques described herein relate to a system, wherein the first sensor element further includes a first gyroscope, wherein the second sensor element further includes a second gyroscope.

In some aspects, the techniques described herein relate to a system, wherein the first sensor element further includes a first magnetometer, wherein the second sensor element further includes a second magnetometer.

In some aspects, the techniques described herein relate to a system, further including: a collector, the collector configured to receive at least one of information generated by the first sensor element and the second sensor element from at least one of the first communications interface and the second communications interface.

For purposes of this summary, certain aspects, advantages, and novel features of the invention are described herein. It is to be understood that not necessarily all such advantages may be achieved in accordance with the particular embodiments of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

These and other features, aspects, and advantages of the disclosure are described with reference to drawings of certain embodiments, which are intended to illustrate, but not to limit, the present disclosure. It is to be understood that the accompanying drawings, which are incorporated in and constitute a part of this specification, are for the purpose of illustrating concepts disclosed herein and may not be to scale.

Figure 1:
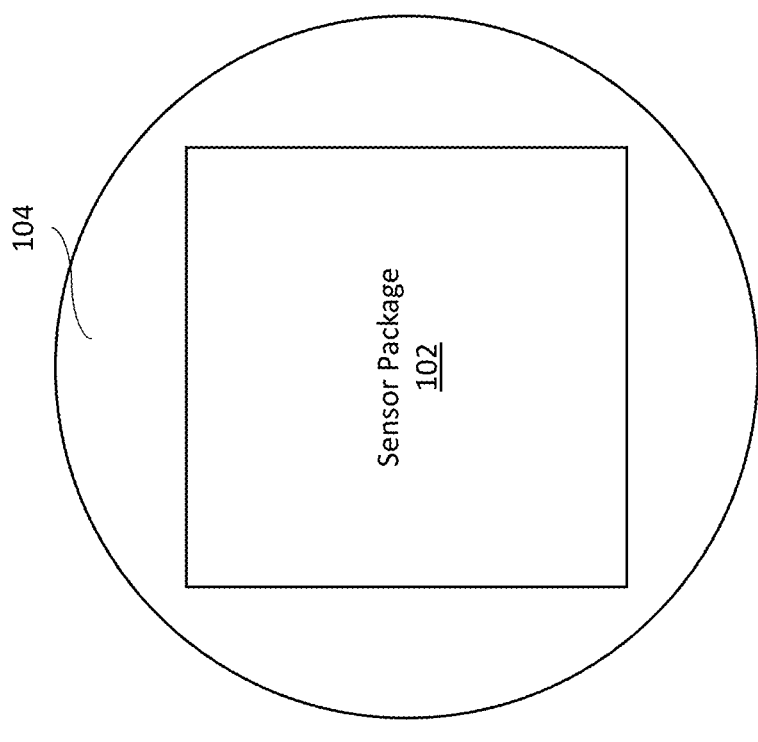
Figure 1:
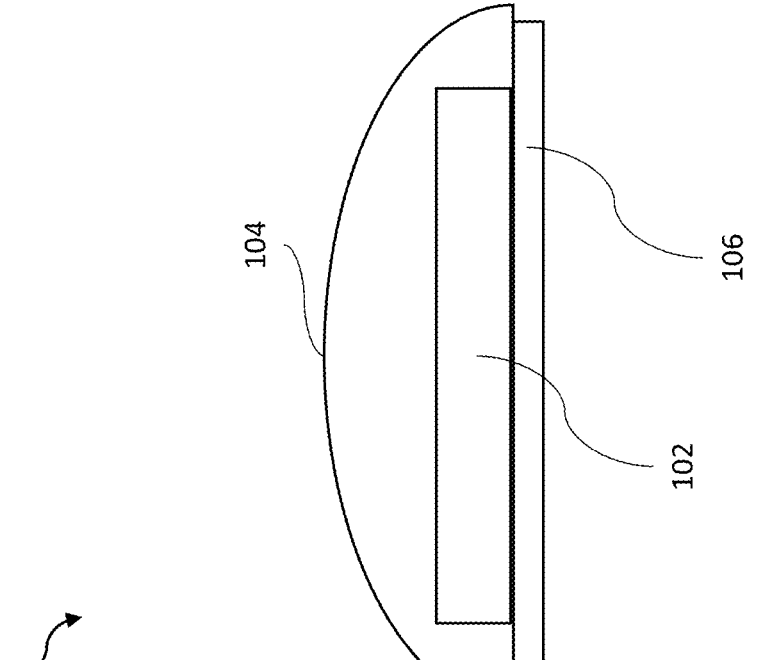

FIG. 1 depicts an example sensor patch according to some embodiments.

Figure 2:
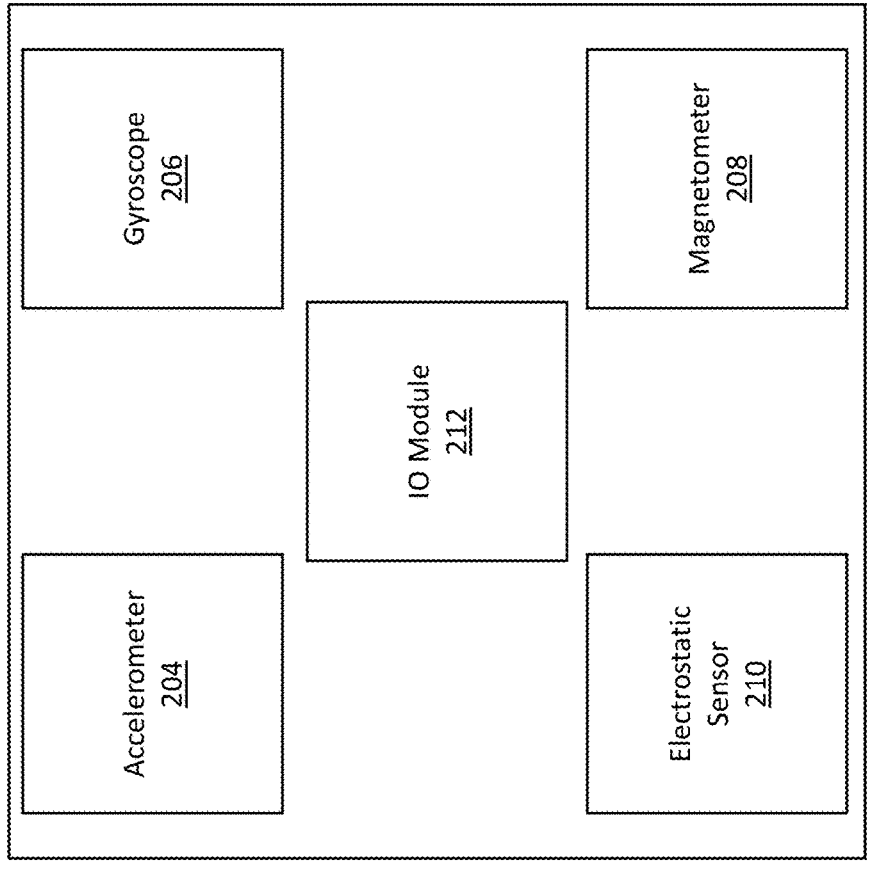

FIG. 2 shows an example sensor integrated circuit package according to some embodiments.

Figure 3:
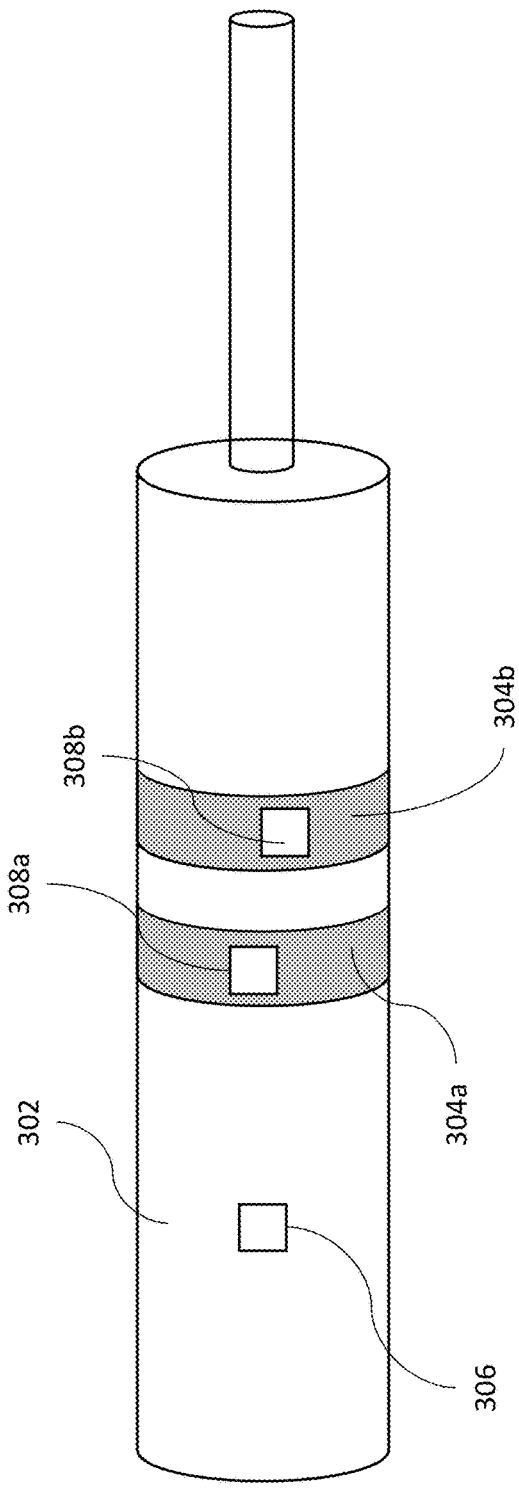

FIG. 3 depicts an example sensor configuration for orientation determination according to some embodiments.

Figure 4:
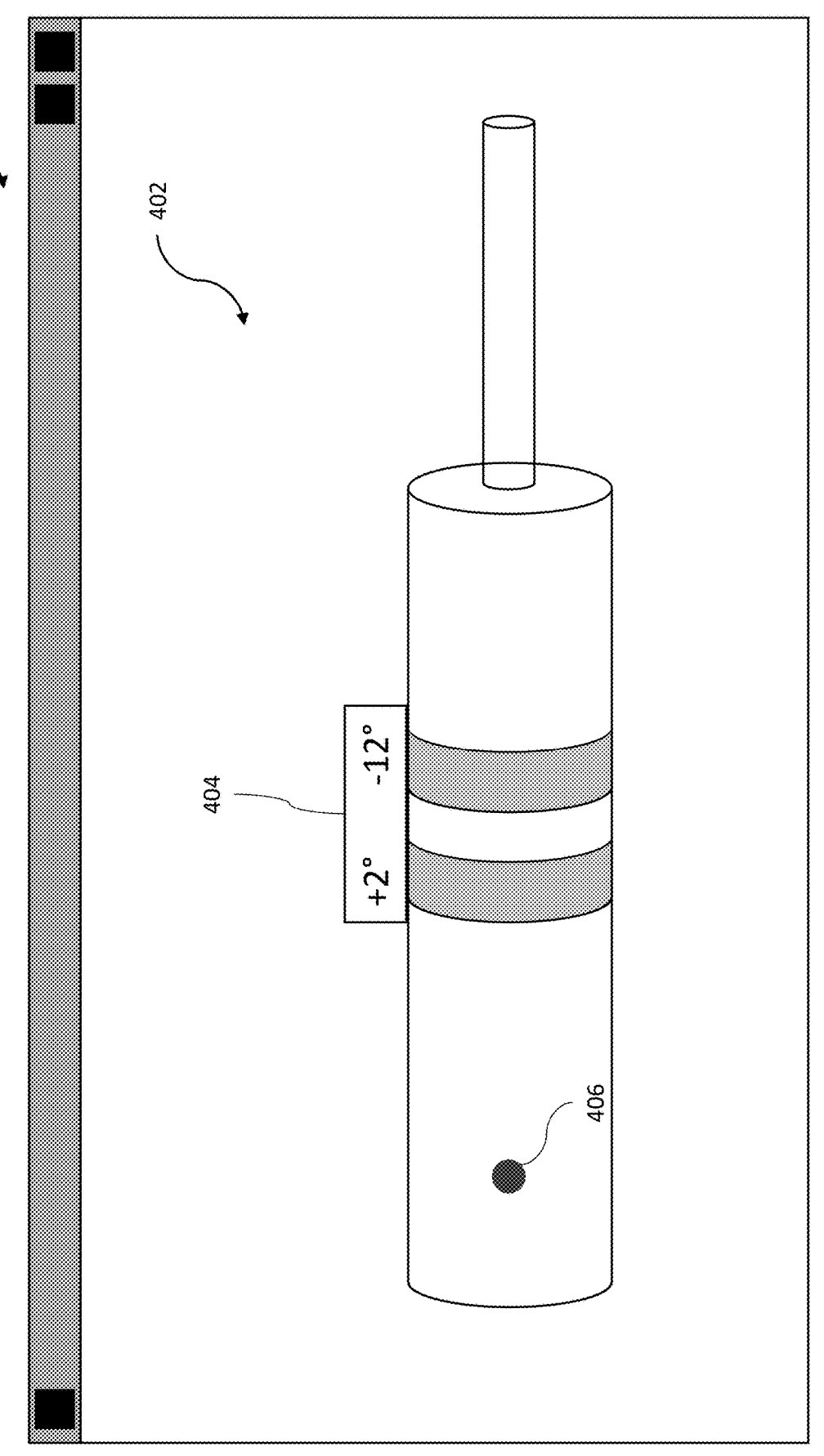

FIG. 4 depicts an example user interface according to some embodiments.

Figure 5:
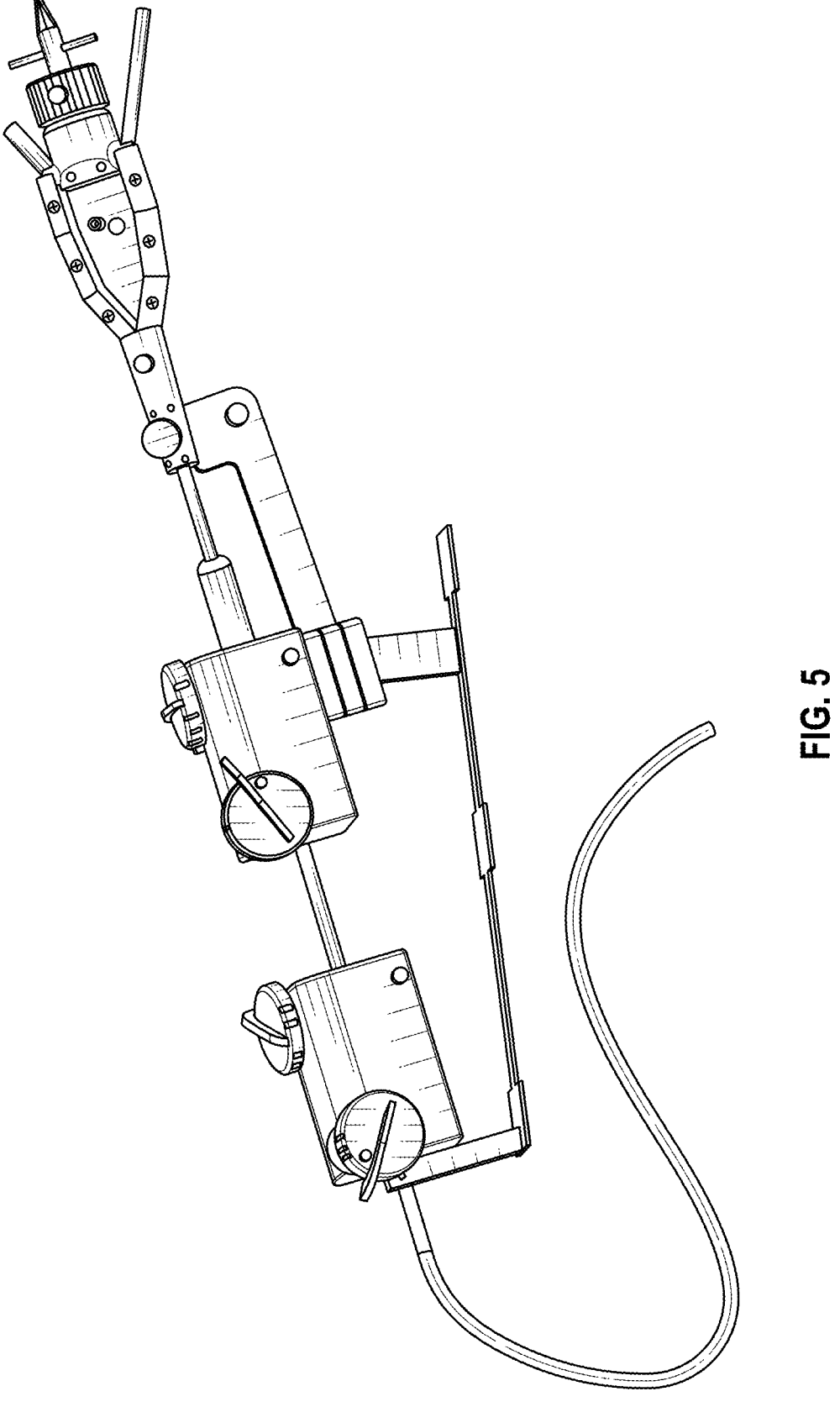

FIG. 5 depicts an example 3D model of a device handle according to some embodiments.

Figure 6A:
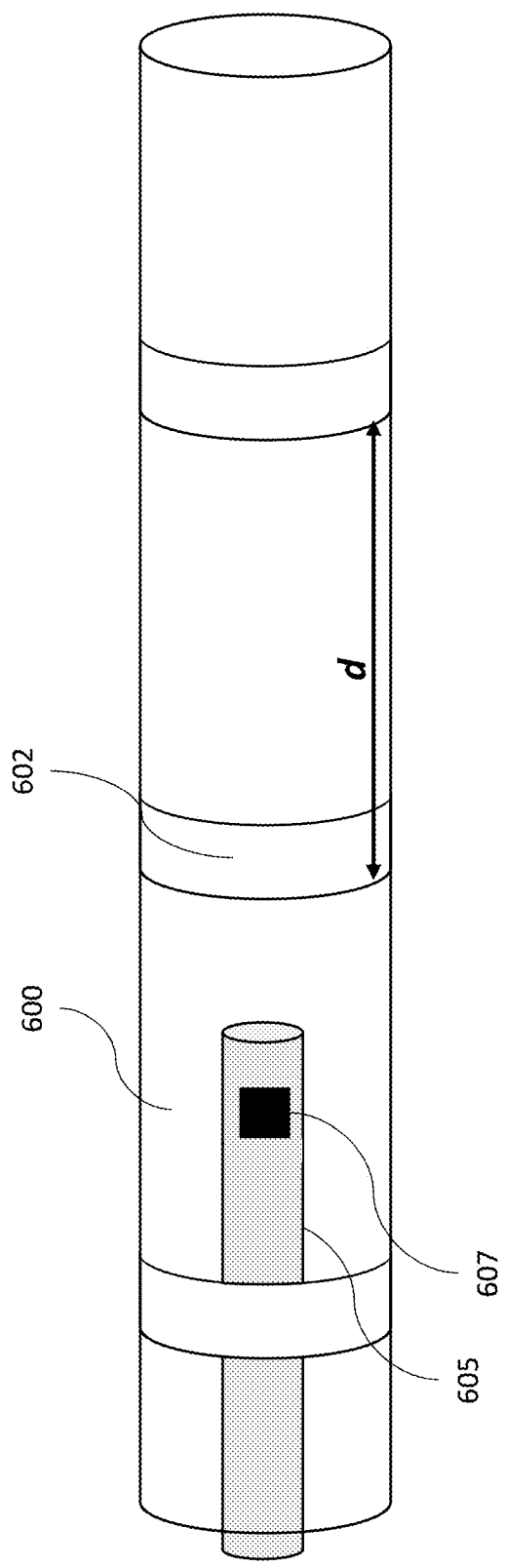

FIG. 6A depicts an example embodiment of a sheath according to some embodiments.

Figure 6B:
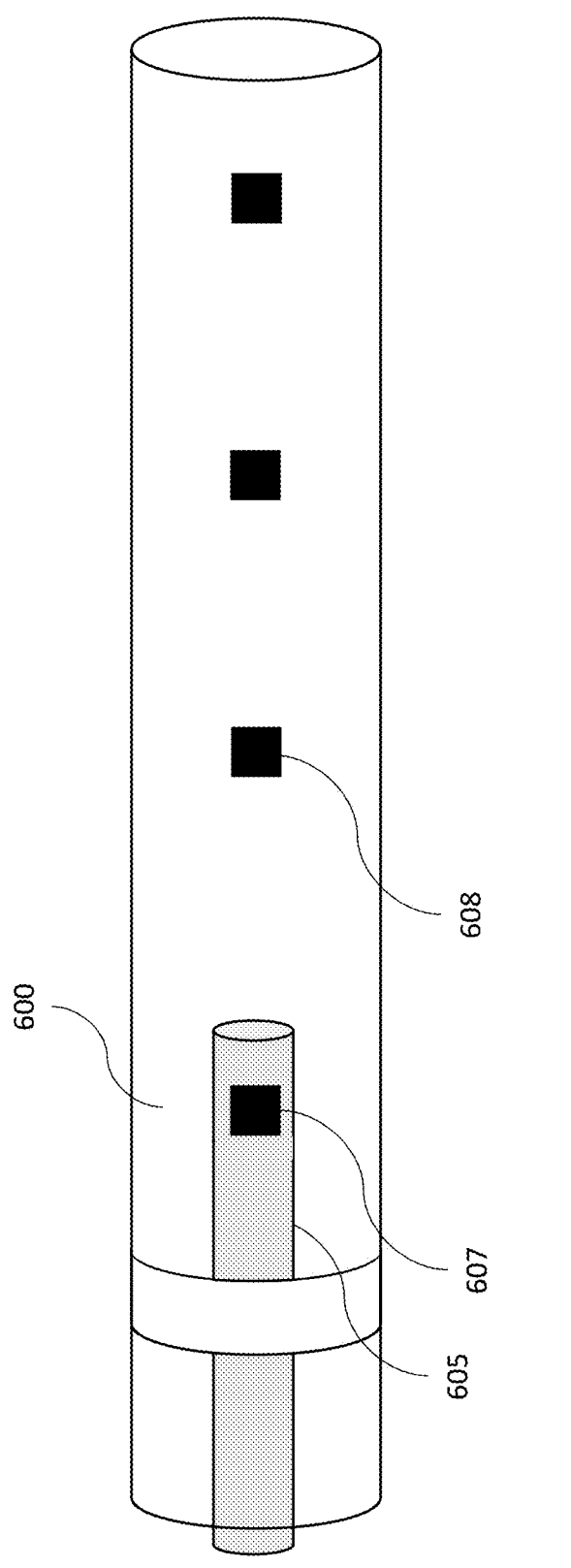

FIG. 6B depicts an example embodiment of a sheath according to some embodiments.

Figure 7:
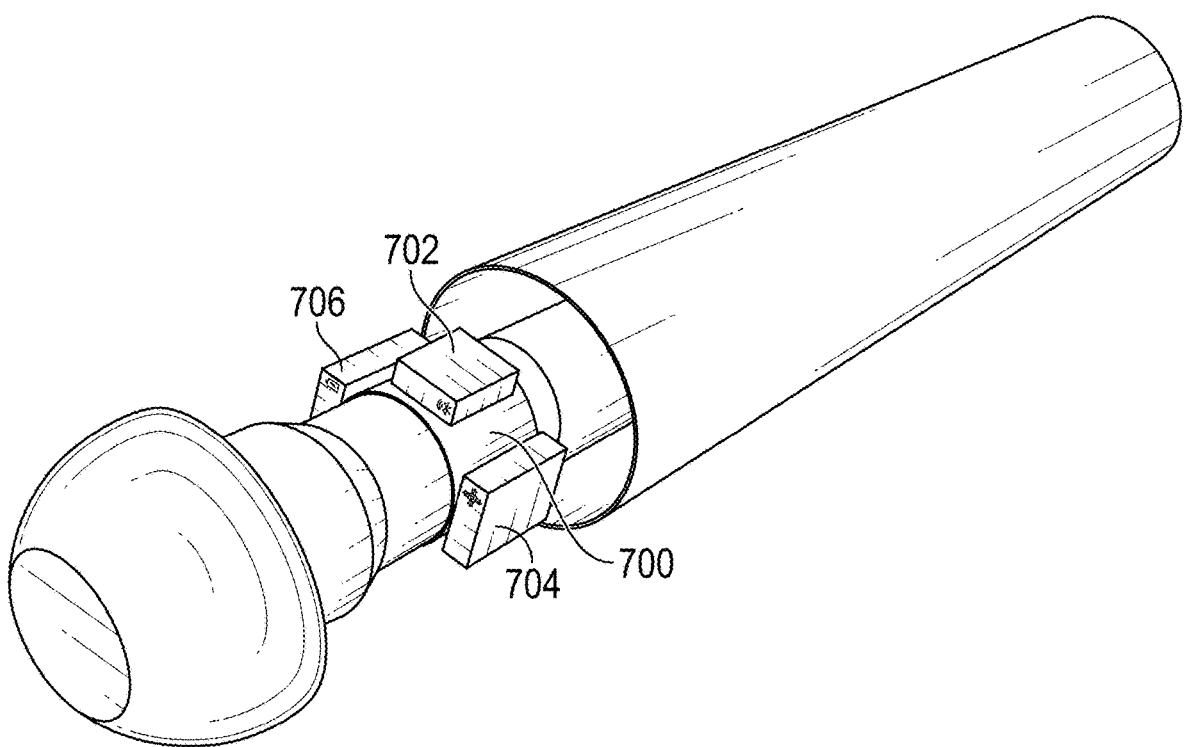

FIG. 7 depicts an example embodiment of a sensor capsule.

Figure 8:
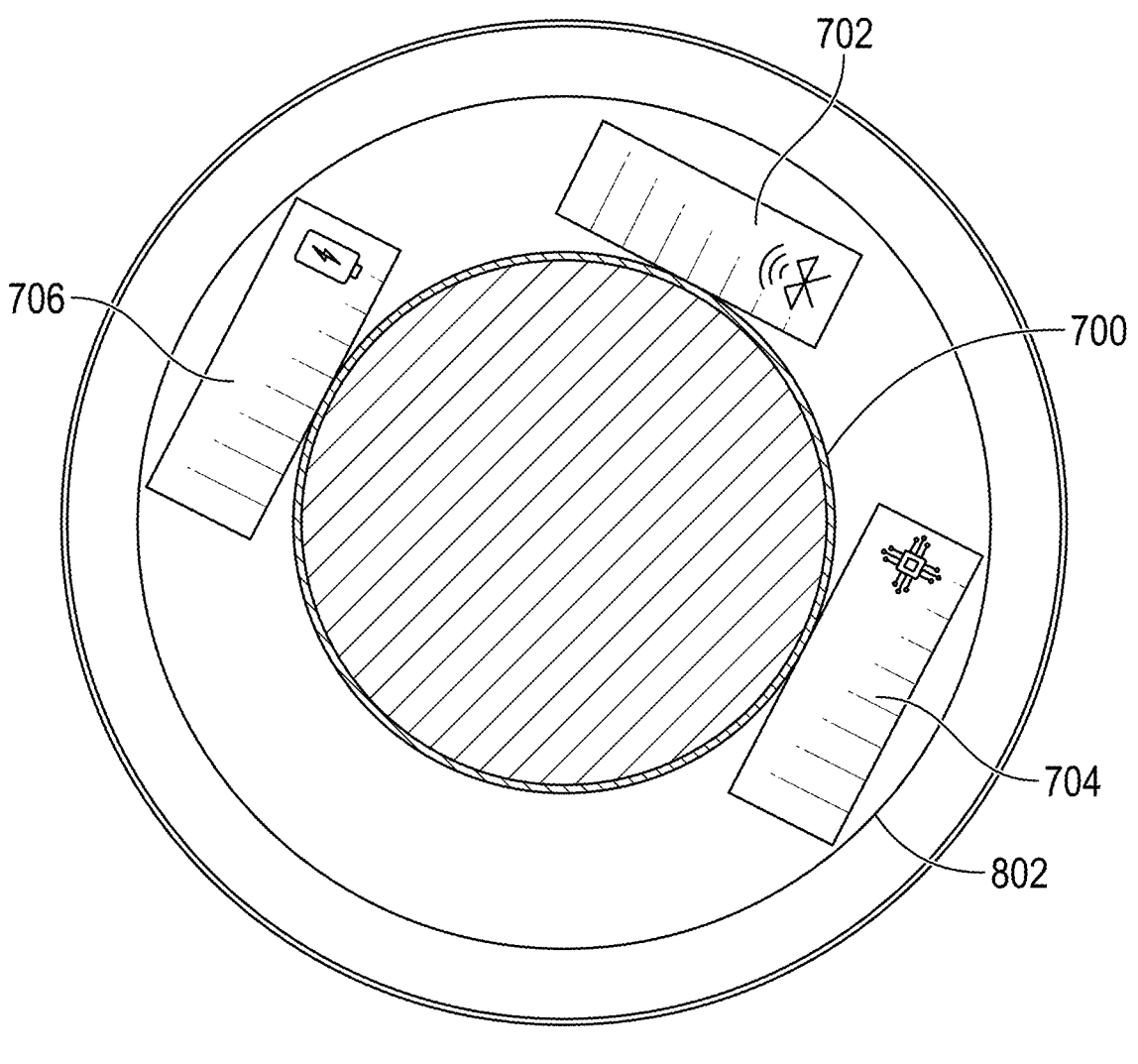

FIG. 8 depicts an end view of an example medical device having an example sensor capsule affixed thereto.

Figure 9A:
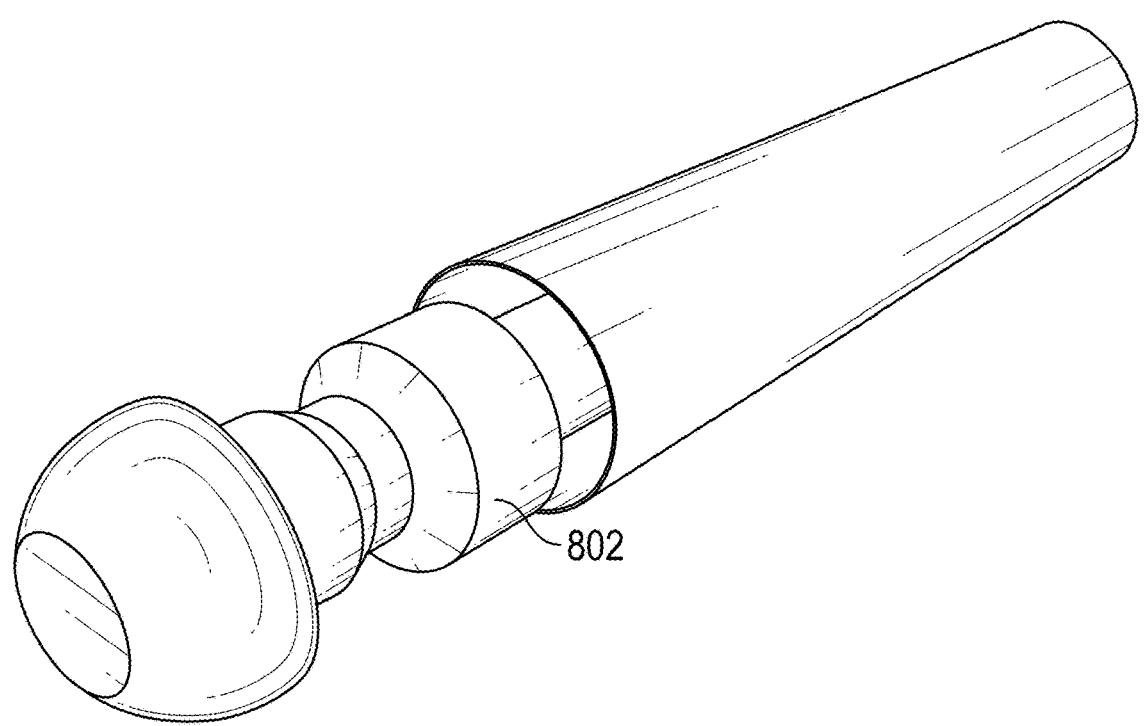
Figure 9B:
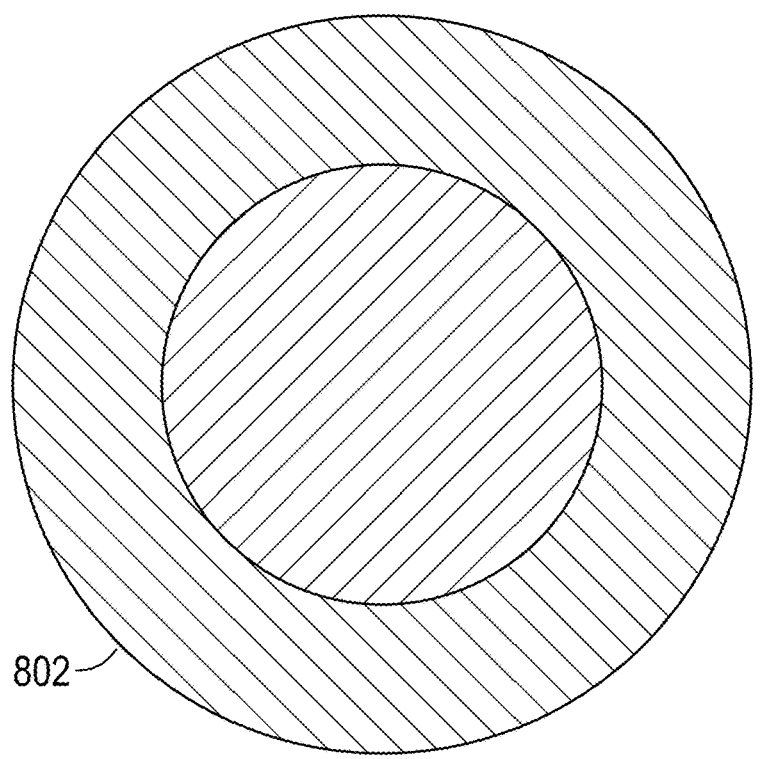

FIGS. 9A and 9B depict an example sensor capsule with a flexible wrap that is placed on a shaft of a medical instrument.

Figure 10:
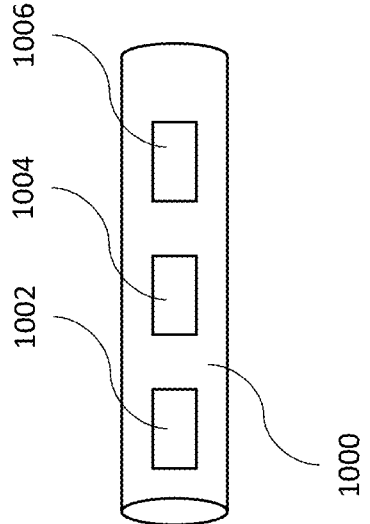
Figure 11A:
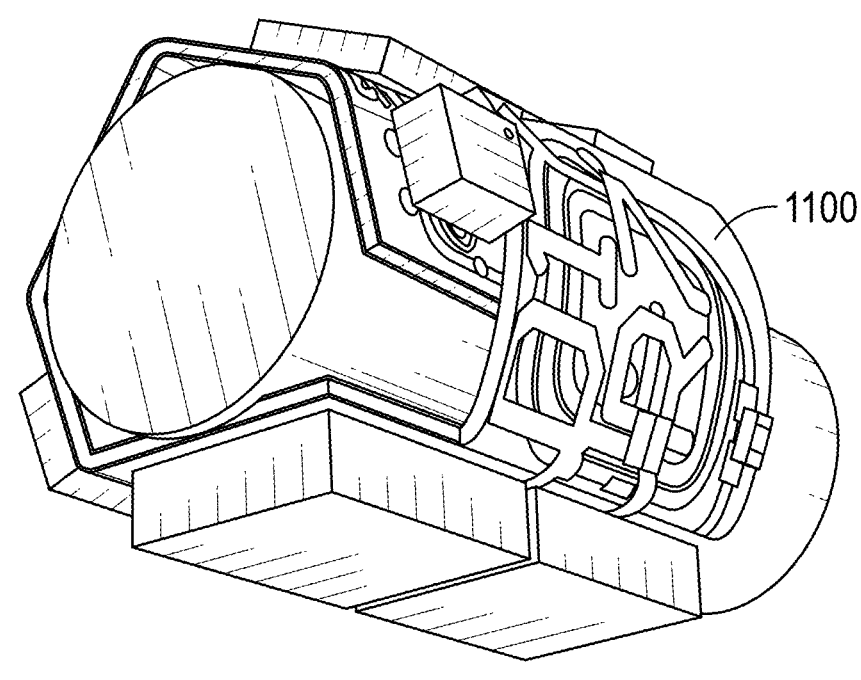
Figure 11B:
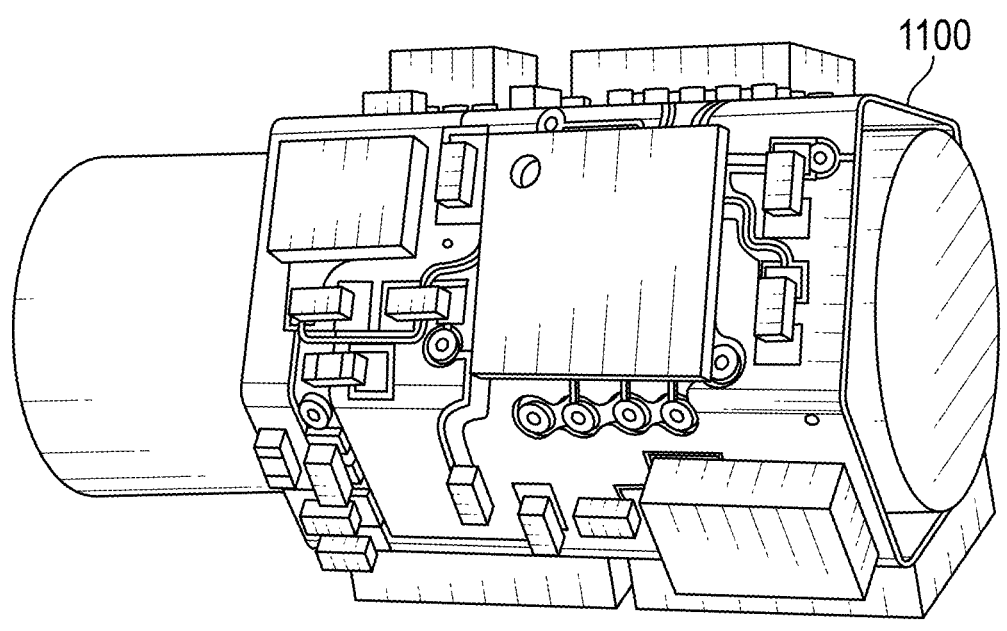
Figures 11C, 11D:
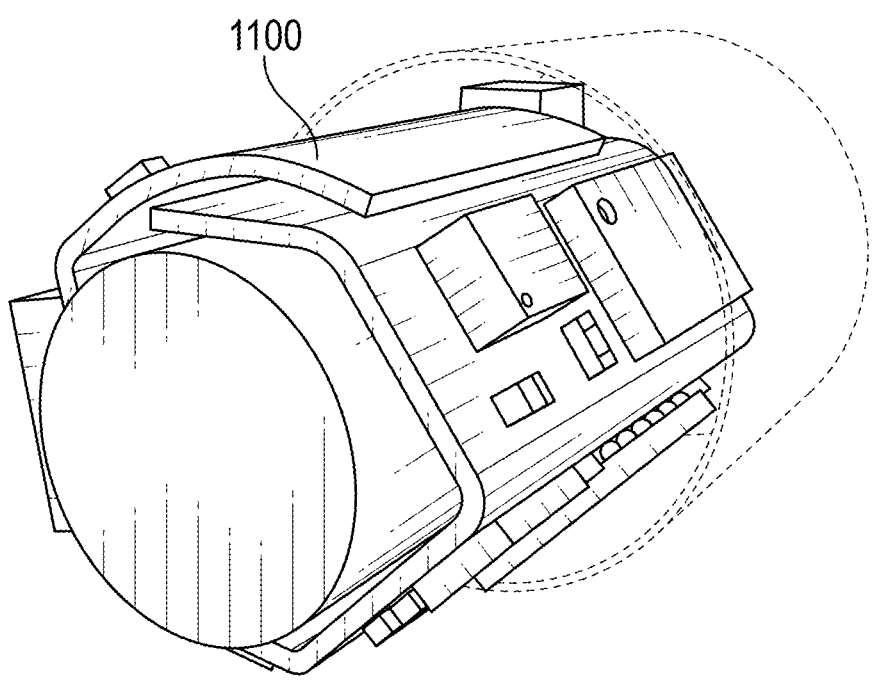

FIG. 10 depicts an embodiment of a sensor capsule with axially-distributed components.

FIGS. 11A-11D show example embodiments of a sensor capsule.

Figures 12A, 12B, 12C:
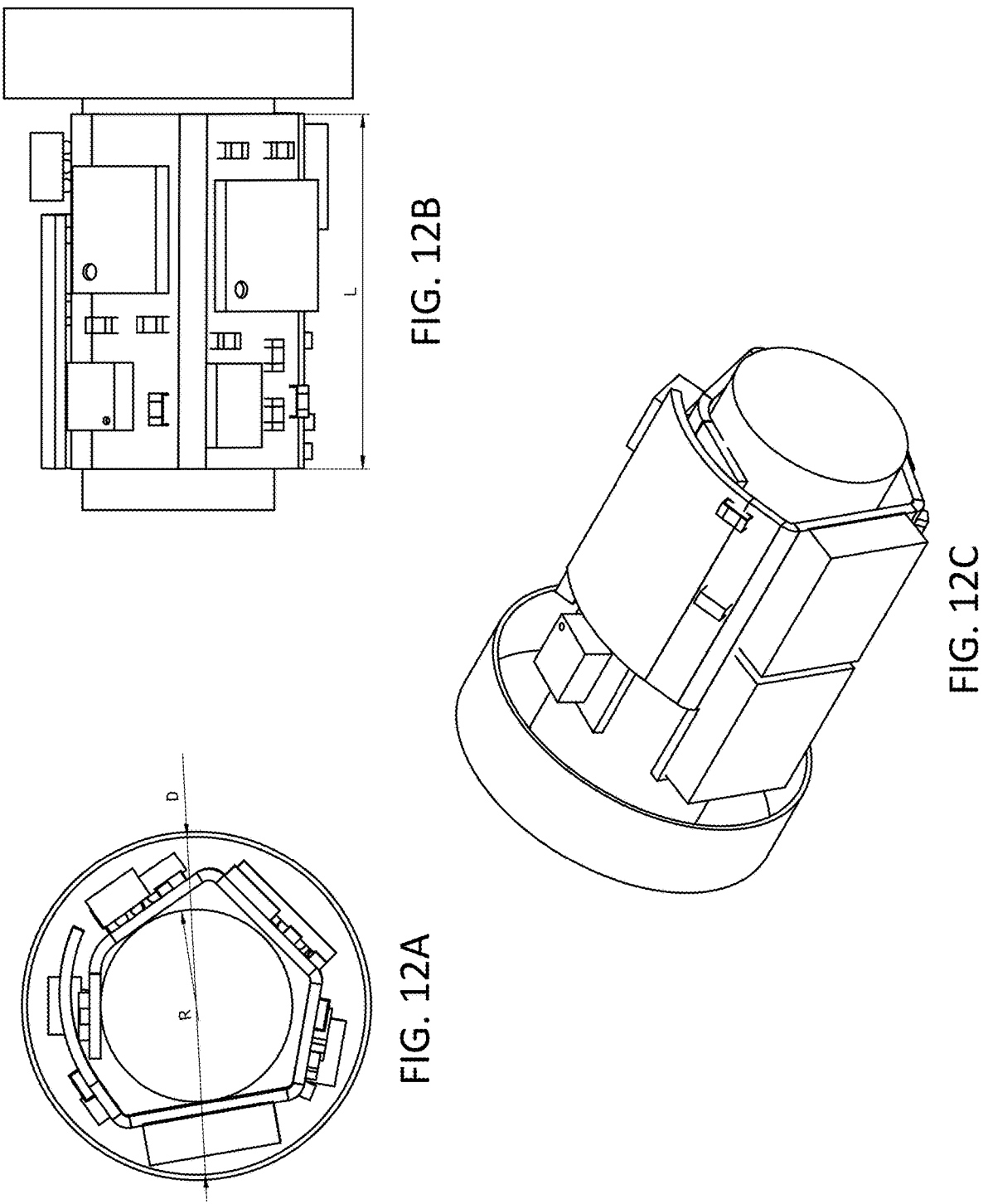

FIGS. 12A-12C show example embodiments of a sensor capsule.

Figure 13:
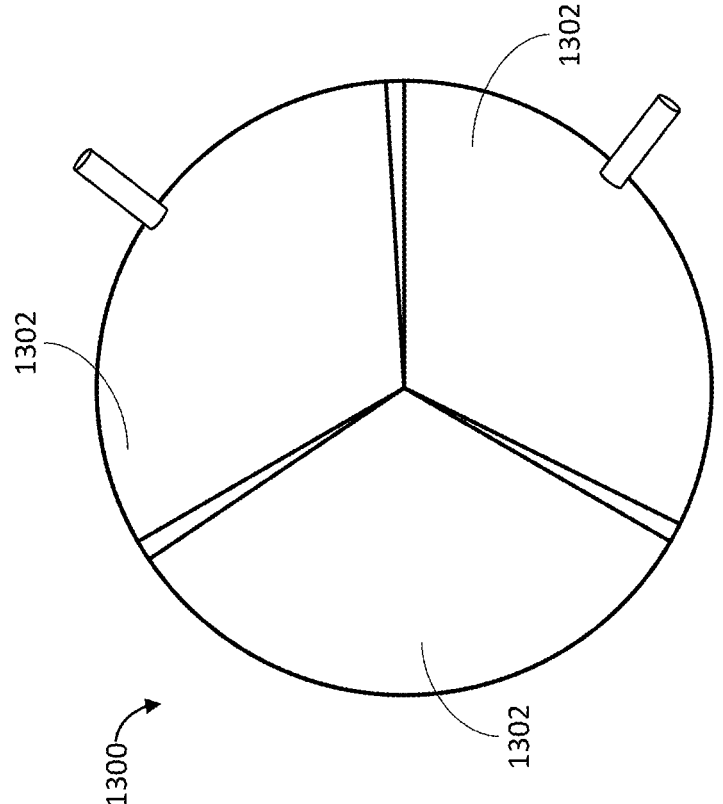

FIG. 13 depicts an example of an aortic valve.

Figure 14B:
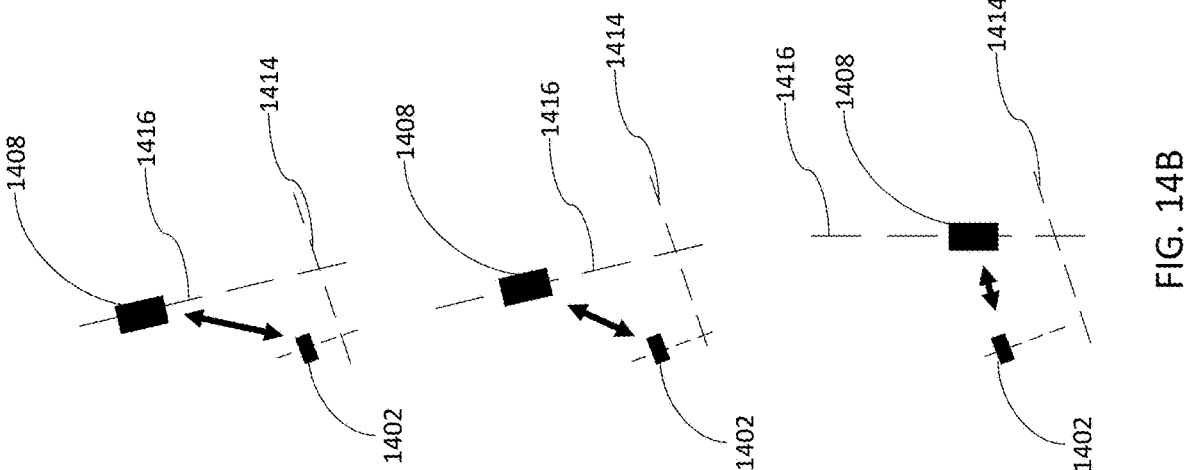
Figure 14A:
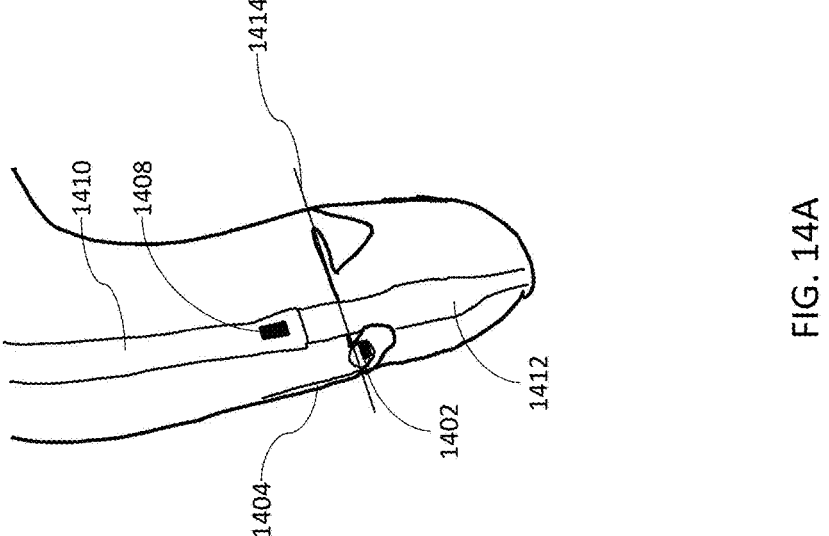

FIG. 14A illustrates an example of a pigtail with a sensor element affixed thereto according to some embodiments herein.

FIG. 14B illustrates the relative position of a sensor elements according to some embodiments.

Figure 15:
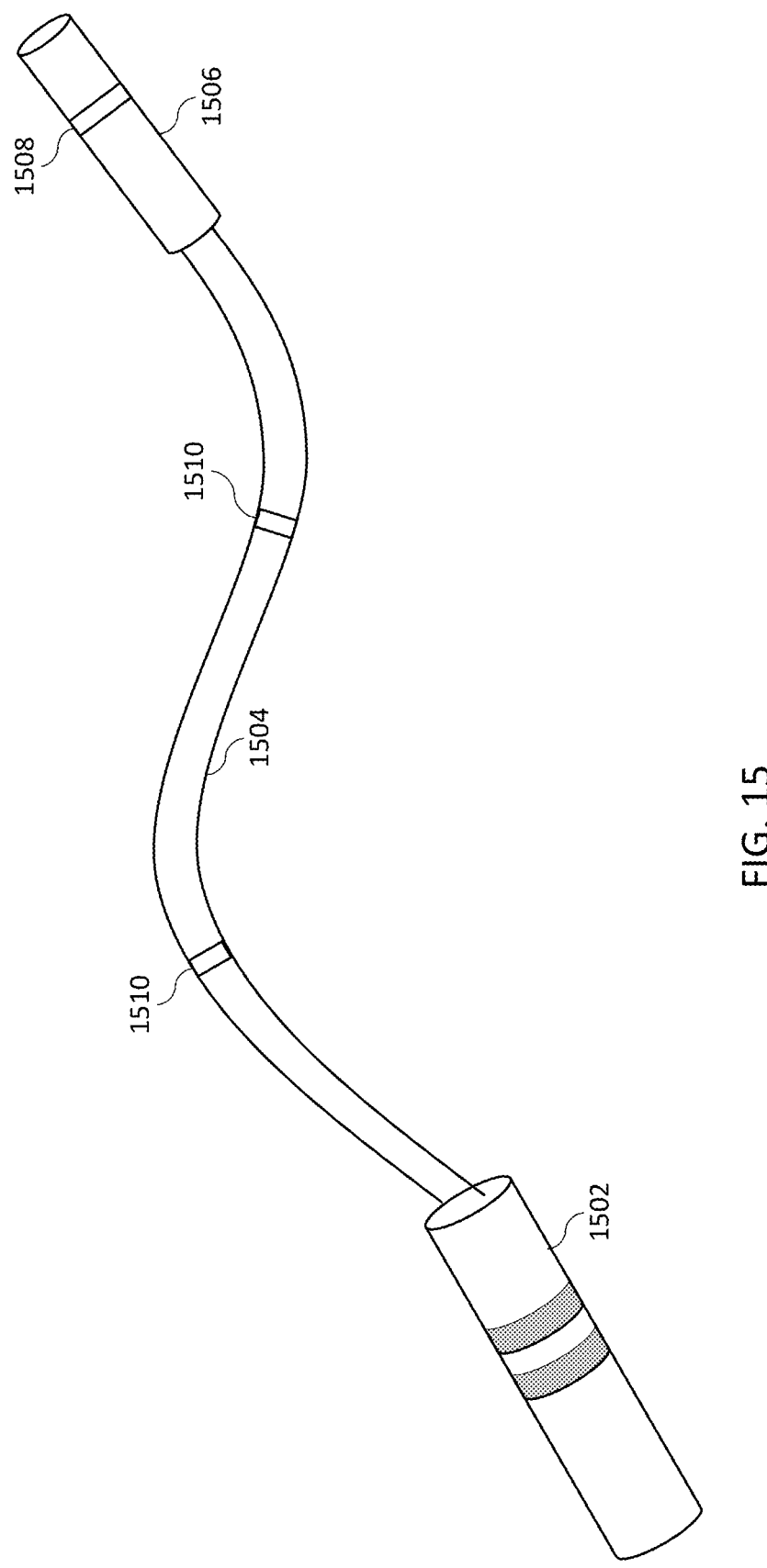

FIG. 15 depicts an example medical device that may be used when performing a procedure such as transcatheter aortic valve replacement.

Figure 16:
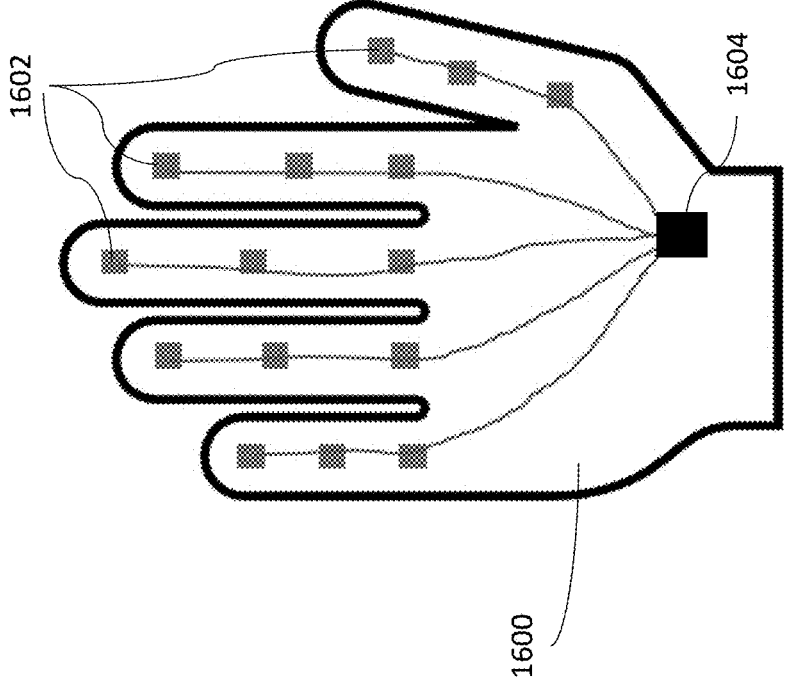

FIG. 16 depicts an example glove according to some embodiments which may be used to track hand and finger movements.

Figure 17:
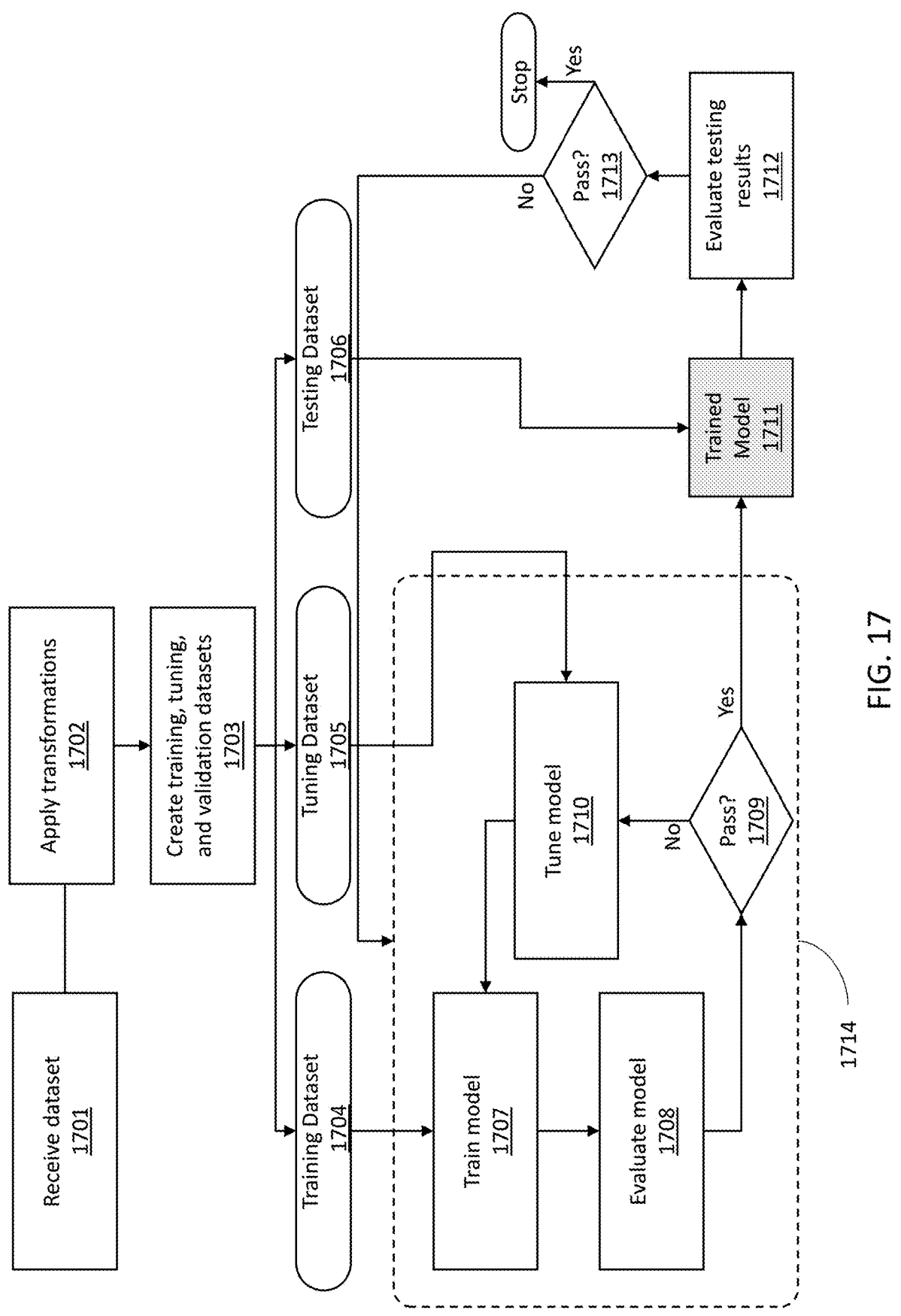

FIG. 17 depicts an example block diagram of a process that may be run on a computing system for training an AI/ML model according to some embodiments.

Figure 18:
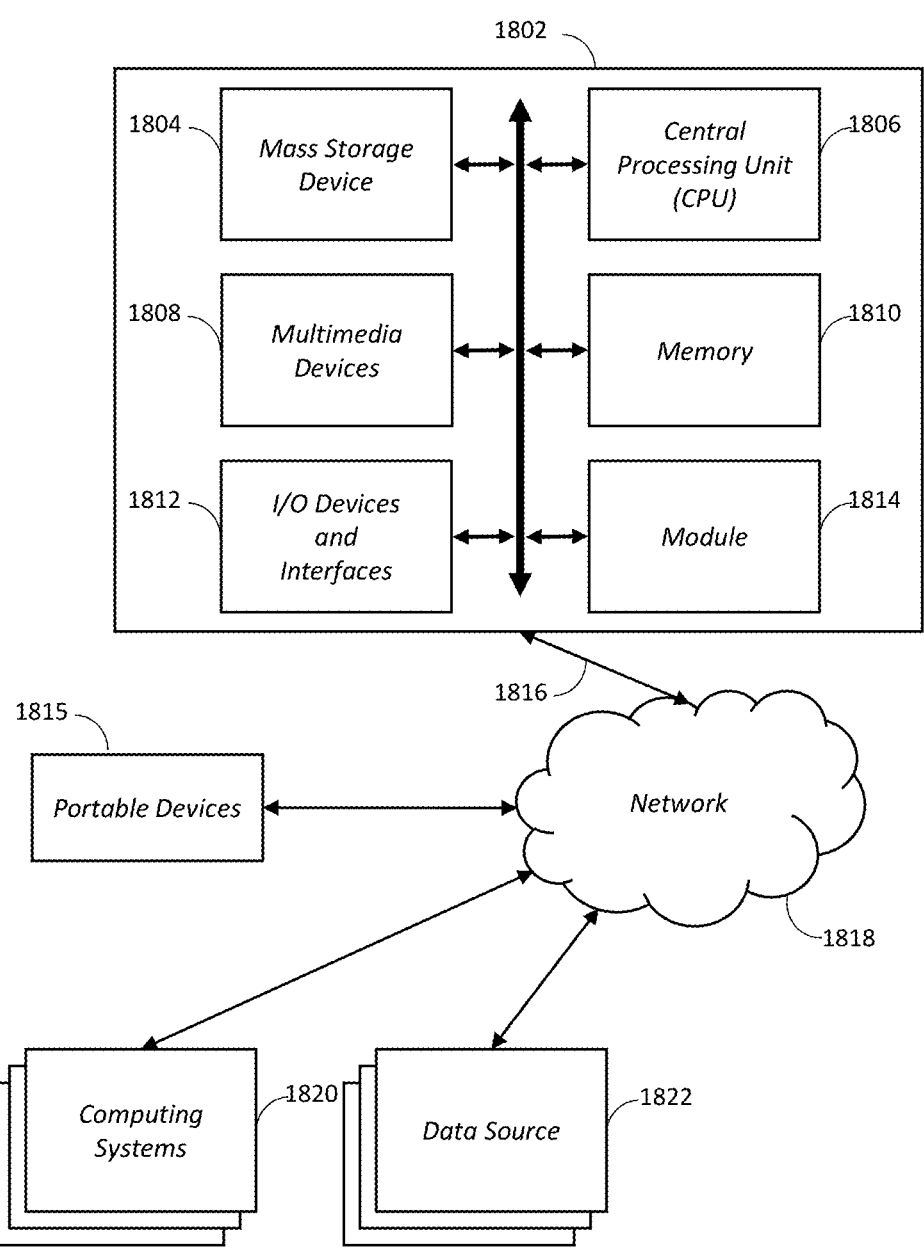

FIG. 18 is a block diagram depicting an embodiment of a computer hardware system configured to run software for implementing one or more embodiments of the systems, methods, and devices disclosed herein.

DETAILED DESCRIPTION

Embodiments of the disclosure will now be described with reference to the accompanying figures. The terminology used in the description presented herein is not intended to be interpreted in any limited or restrictive manner, simply because it is being utilized in conjunction with a detailed description of embodiments of the disclosure. Furthermore, embodiments of the disclosure may include several novel features, no single one of which is solely responsible for its desirable attributes or essential to practicing the embodiments of the disclosure herein described. For purposes of this disclosure, certain aspects, advantages, and novel features of various embodiments are described herein. It is to be understood that not necessarily all such advantages may be achieved in accordance with any particular embodiment. Thus, for example, those skilled in the art will recognize that one embodiment may be carried out in a manner that achieves one advantage or group of advantages as taught herein without necessarily achieving other advantages as may be taught or suggested herein.

Introduction

Surgical outcomes can be highly variable. Variation in outcomes can arise from many sources such as the patient's own health and lifestyle (e.g., comorbidities, exercise routines, diet, smoking, adherence to post-operative instructions, and so forth) and variations in how surgical procedures are performed. Presently, there is a lack of meaningful data that can tie surgical outcomes to details of how a procedure was performed. Thus, it may be advantageous to implement hardware and/or software components that allow movements during surgery to be tracked. For example, it may be helpful to track the orientation of a surgical device's handle. In some embodiments, the motion of one or more components of the surgical device can be tracked (for example, a handle may have one or more moveable parts such as knobs, levers, and so forth for manipulating the surgical device) is moving. Such tracking can provide a valuable record that can be used to inform future procedures, to make decisions about a current procedure, and so forth.

The ability to track movements of instruments, operating room personnel, or both during surgical procedures could offer many benefits. Surgeons may be able to review their own procedures and determine changes to how they perform procedures that may improve patient outcomes, reduce surgery times, and so forth. In some embodiments, a tracking system may be able to operate in real time or nearly real time such that the tracking system can be configured to alert the surgeon if the surgeon is performing movements that could increase the risk of negative outcomes. In some embodiments, the tracking system can be configured to increase a data collection rate upon detecting that a surgeon is performing movements that could increase the risk of negative outcomes, upon detecting that the surgeon has reached a particular stage or step in the procedure, and so forth. For example, if movements are tracked throughout a surgical procedure, the tracking can be configured to determine a current step, a future step, and/or the like based at least in part on the movements, for example based on how far a portion of a surgical instrument has been inserted into the patient, manipulations of the surgical device (for example, by moving a handle of the surgical device, moving a knob, lever, etc., of the surgical device, and so forth). In some embodiments, the surgeon or a member of the surgical team can indicate a current step in a surgical procedure. For example, a computer system for surgical tracking can be configured to accept user input that indicates a current stage of a surgical procedure, for example a current step of a surgical plan. In some embodiments, the surgeon or a member of the surgical team can update the surgical plan based on events that occur during the procedure, such as encountering greater blockage than expected, greater levels of bleeding than expected, and so forth.

In some embodiments, a particular step being detected as a current or future step can trigger additional data collection from other sources. For example, in some embodiments, camera, fluoroscope, or sensor data may not be collected, but the system may begin collection upon detecting increased risk or a particular stage in the procedure. In some embodiments, data can be collected throughout the procedure, but a rate of data collection can be increased at particular steps or upon certain detections, which can enable capture of an entire procedure or a substantial portion of the procedure while limiting storage and processing requirements. For example, a sudden acceleration or rotation detected by a sensor can indicate higher risk, for example because a catheter became twisted, kinked, blocked by an obstruction, and so forth.

In some embodiments, movement tracking data may be stored and pooled with other tracking data from other procedures. In some embodiments, the data can be combined with patient outcome information, patient demographic information, and so forth to enable outcome prediction, to make recommendations about surgical procedures, and so forth. While a surgeon may review individual procedures to gain some insight into how best to perform future procedures, it can be advantageous to consider many procedures conducted by many different surgeons. For example, a single surgeon may only rarely encounter a particular combination of factors that influence the procedure and its outcome. Surgical outcomes can be influenced by a wide variety of factors, and surgeons may be unaware of some factors, the interplay between factors, and so forth. In some embodiments, the data may be used to train artificial intelligence (AI) or machine learning (ML) predictive models that can, for example, estimate the probability of a successful outcome given specific procedural data and information about the patient's health. In some embodiments, an AI/ML model (or combination of models) can be used to recommend particular surgical approaches for a patient. In some embodiments, the data may be used to aid in training surgeons and other operating room staff, for example by identifying common problem areas, comparing the characteristics of different procedures, and so forth.

In some embodiments, such information may be used by a hospital or other healthcare facility for analytics purposes. For example, a healthcare facility may track the efficiency of procedures, patient outcomes over time, costs, and so forth. In some embodiments, healthcare facilities and surgeons may use tracking data from past procedures when confronted with a malpractice claim. For example, a healthcare facility or physician group may review tracking data about a procedure to determine if the procedure was performed correctly. Thus, for example, the healthcare facility or physician group can determine whether or not to settle a malpractice claim, an appropriate settlement amount, to whom liability (if any) should be assigned, and so forth.

Surgical Tracking

Tracking movements during a surgical procedure can provide valuable information. In some embodiments, sensor elements may be attached at various locations on surgical instruments (for example, on handles, knobs, distal ends of catheters, and so forth). In some embodiments, surgical personnel may have one or more sensor elements affixed to them (for example, a surgeon might wear gloves equipped with motion sensors that can be used to monitor finger movements). In some embodiments, sensor elements may be used for tracking the location and usage of various surgical devices. For example, sensor elements may be used to track how often a surgical device is picked up. In some cases, sensor elements attached to surgical devices may enable detailed information to be gathered about each device's usage. For example, sensor elements may enable tracking of how many times a movable part has been manipulated, which may enable a healthcare facility to more accurately determine maintenance and replacement schedules. For example, maintenance or replacement can be based on actual usage rather than adhering to a fixed timing schedule or waiting until a device fails, which can reduce costs.

In some embodiments, sensor elements may be used to collect detailed data about surgical procedures. For example, sensors attached to a surgical instrument handle may enable a surgeon to know how much a moveable part of a surgical instrument handle is rotating in real time or nearly real time. Sensor elements may also be located on, for example, the distal tip of a catheter and/or another location on a specific medical device. This can enable a surgeon to know, for example, the translation and rotation of the shaft and distal tip. This can be particularly important because manipulations performed using a handle may not translate directly into motion of the shaft and distal tip. For example, a portion of the catheter can be twisted, kinked, encounter an obstacle that prevents free movement, and so forth. While in some embodiments, sensor elements may be applied directly to surgical instruments (for example, onto fixed and moveable parts of a handle, embedded in the tip of a catheter, and so forth), in other embodiments, such sensor elements may not be used or may be used in addition to other tracking methods. For example, in some embodiments, the movements of a device handle (and/or rotatable or otherwise moveable parts of the device handle) can be monitored using cameras. In some embodiments, a device handle may have one or more fiducials to aid in tracking. In some embodiments, computer vision and/or artificial intelligence systems may be used to track movements. In some embodiments, tracking of instruments inside the patient's body (e.g., a catheter shaft and tip) may be accomplished using fluoroscopy rather than or in addition to using sensors that are incorporated into the surgical device, although as discussed herein, the use of sensors in or on a surgical device can provide many benefits.

In some embodiments, surgeons may map the volume of a vessel inside the patient by inserting a device into a suitably designed sheath. For example, a surgeon can map blood vessels, a heart chamber, or any other cavity inside the body. Advantageously, such mapping may be accomplished without the use of external patches on the patient, which can shift during mapping, leading to inaccurate results. In some embodiments, sensors may be attached to gloves worn by a surgeon, and the movement of the surgeon's hands and fingers can be monitored in real time or nearly real time and stored for later review, as discussed in more detail below.

A sensor element can include, for example, microelectromechanical systems (MEMS). A sensor element can include a gyroscope, an accelerometer, or both to enable a system to determine a relative orientation, position, and so forth of the sensor. In some embodiments, the sensor element can have on-board processing capabilities for determining relative orientation, position, and so forth. In some embodiments, the sensor element can include a magnetometer, which may be used to determine orientation with respect to an external reference (for example, a magnetic pole of earth such as the north pole or south pole). In some embodiments, a processing element can be included in a sensor package and can be configured to receive information from the sensor element.

While these sensor elements can provide information about the orientation and movement of a surgical device, they offer limited positional information. That is, the sensor elements can be used to determine the motion of an object, but they may not be able to provide absolute positioning information. While external information can be used to aid in determining positioning (for example, if a starting location is known, a current position can be determined from the starting position and the measured movements of the sensor element), even small errors in positioning determination can be impactful for surgical procedures. In some embodiments, electrostatic sensing may be used to aid in determining absolute positioning. Electrostatic sensors can be obtained from a variety of sources, such as Qvar-enabled sensors from STMicroelectronics of Geneva, Switzerland.

Sensor elements can be included in various sensor packages, which can include additional hardware such as, for example, communications, power, and so forth. Sensor packages can include, for example, patches, capsules, and so forth as described herein. In some embodiments, sensor elements can be embedded in, for example, a sheath for inserting a catheter into a patient, as described herein. In some embodiments, the materials, attachment mechanism, electronic hardware, and so forth can be selected based on a use for the sensor package. For example, a sensor package for use on a handle of a surgical device should preferably be small and unobtrusive to avoid interfering with the surgeon. A sensor package that can be inserted into the body can be designed differently, for example based on the diameter of openings in the body through which the sensor package can pass. Materials for sensor packages intended for internal use can be selected to be biocompatible, to prevent exposure of sensitive electronics to fluids, and so forth, as described herein.

FIG. 1 depicts an example patch 100 according to some embodiments. The patch The patch 100 contains a sensor element 102 that can be enclosed in a shell 104. An adhesive 106 can be affixed on a bottom surface of the shell. The patch 100 can be affixed by the adhesive 106 to any portion of an instrument that does not enter the body of a patient or that is not exposed inside the body of the patient. For example, the patch 100 may be affixed to a handle of a surgical instrument. In some embodiments, the sensor element 102 may continuously and/or periodically provide raw data to a computer, for example by a USB cable, Bluetooth connection, Wi-Fi, Bluetooth Low Energy, NFC, or other suitable communication interface. As mentioned briefly above, in some embodiments, a patch 100 can include hardware that enables on-board processing of raw data to determine position, pose, or the like. In some embodiments, the patch 100 may also include a battery. In some embodiments, the battery may be rechargeable so that the patch 100 can be recharged and reused multiple times. In some embodiments, a non-rechargeable battery may be used and the patch 100 may be discarded after use. In some embodiments, the patch 100 may be configured to withstand sterilization procedures (e.g., exposure to elevated temperatures and/or pressures).

In some embodiments, the patch 100 may be applied to any suitable device. In some embodiments, a camera can be used to capture images of a surgical prep table and computer vision or artificial intelligence may be used to recognize devices with patches applied. For example, a machine learning or artificial intelligence model can be trained in a supervised manner using tagged images of surgical equipment with patches applied to them. In some embodiments, patches may have specific identifiers that are linked to specific devices. For example, software may be provided that allows a user to enter an identifier (e.g., a serial number, MAC address, IP address, or the like) for a patch and to associate a particular patch with a device, and optionally with a location on a device (e.g., a patch may be associated with a knob that allows movement left and right, while another patch may be associated with a knob for extension/retraction of a portion of a device).

FIG. 2 shows an example sensor element 102 according to some embodiments. The sensor element 102 includes an accelerometer 204, a gyroscope 206, a magnetometer 208, an electrostatic sensor 210, and an input/output (IO) module 212. The sensors 204, 206, 208, and 210 can be used to determine motion of an object, orientation of an object, and the position of an object with respect to an external reference. In some embodiments, the magnetometer 208 may not be present or may not be utilized. In some embodiments, the electrostatic sensor 210 may not be present or may not be utilized. In some embodiments, the gyroscope 206 may not be present or may not be utilized. The IO module 212 may include wireless and/or wired communications. For example, the IO module 212 may communicate using Bluetooth, WiFi, Zigbee, Bluetooth Low Energy, NFC, or another suitable protocol. Preferably, the communications method uses a low amount of energy so that power consumption is minimized and battery life can be maximized, which can be especially important if the sensor element 102 is used while connected to a battery rather than to a wired power source. It will be appreciated that in some embodiments, various components of the sensor element 102 can be integrated into a single electronic device. For example, an integrated circuit can include accelerometer, gyroscope, magnetometer, and/or electrostatic sensing functionality. In some embodiments, the sensor element 102 can comprise multiple components. For example, IO module 212 can be a different physical component from some other components.

The sensor element 102 may be embedded or enclosed in a patch, such as the patch 100, or may be installed directly on or in a surgical device. For example, the sensor element 102 may be installed in the distal end of a catheter so that movements of the catheter can be tracked. In such a configuration, the sensor element 102 may use wired connections for power delivery and/or signal transmission. Similarly, if the sensor is installed in a non-moving part of the handle of a surgical instrument, it may be preferable to use wired communications and power delivery, although in some cases it may still be advantageous to provide battery power and/or to use wireless communications. In some embodiments, if the sensor element 102 is placed on or in a portion of a surgical instrument that will enter a patient's body (e.g., if the sensor element 102 is included in a sensor package that is intended to enter the patient's body), the sensor element 102 can be placed in or on a portion of the surgical instrument that is not exposed directly to the patient, for example to prevent the sensor element 102 coming off of the surgical instrument and becoming free inside the patient's body. For example, in the case of a patch 100, an adhesive could weaken due to rubbing of the patch 100 against the patient, exposure to bodily fluids, and so forth, causing the patch 100 to shift or become free of the surgical instrument.

In some embodiments, the IO module 212 may be configured for two-way communication, which may for example enable some configuration of the sensor element 102. For example, in some embodiments, the IO module 212 can use two-way communication for calibration, pairing to other devices, establishing connections to other devices, and so forth. In some embodiments, the IO module 212 may be configured for one-way communication. That is, the IO module 212 may be configured so that it only transmits signals from the sensors to an external device such as a computer or other receiver. For example, the sensor element 102 can be preprogrammed and/or pre-calibrated and end users may not perform programming and/or calibration of the sensor element 102. In some embodiments, there can be a separate method for configuring and/or calibrating the sensor element 102, for example using a different interface than the IO module 212. In some embodiments, the IO module 212 may be part of a same integrated circuit as the sensors. In some embodiments, the IO module 212 may be a separate integrated circuit.

In some embodiments, the sensor element 102 may be used for orientation applications, for example on a device handle. In some embodiments, the sensor element 102 can be used for determining pose. FIG. 3 depicts an example configuration for orientation determination according to some embodiments. As depicted in FIG. 3, a device handle 300 has a fixed portion 302, a first rotatable portion 304a, and a second rotatable portion 304b. A patch 306 (which may be the patch 100 of FIG. 1) may be affixed to the fixed portion 302. Patches 308a and 308b (which may be the patch 100 of FIG. 1) may be affixed to the rotatable portions 304a and 304b, respectively. In some embodiments, the patch 306 may be permanently or semi-permanently affixed to the handle 300 and may be connected to wired power and/or data transmission lines. In some embodiments, the patch 306 and/or other patches such as the patches 308a and 308b can instead comprise, for example, a sensor module embedded in the handle 300. In some embodiments, the patches 308a and 308b that are affixed to the rotatable portions 304a and 304b may be battery powered and may communicate wirelessly, although in some embodiments a device handle such as the device handle 300 may have internal wiring that can facilitate wired connections of the sensors that are disposed on rotatable or otherwise moveable portions of a device handle. In some embodiments, inductive coupling can be used to provide power, data transfer, or both. For example, in some embodiments, near field communications (NFC) can be used for various purposes, such as establishing connections, transmitting data, and so forth. While FIG. 3 illustrates patches disposed on rotatable portions, it will be appreciated that patches can be applied to any fixed or moveable portion of a handle or other control mechanism for a surgical instrument, such as toggles, joysticks, buttons, or any other mechanical interface for manipulating the surgical instrument.

In some embodiments, the patch 306 may be connected to a computer through a cable (for example, via USB), while in other embodiments, the patch 306 may communicate wirelessly. The patches 308a and 308b may communicate with the patch 306 via a wireless protocol (for example, WiFi, Bluetooth, Bluetooth Low Energy, Zigbee, radio frequency communication, and so forth) In some embodiments, communications can occur via wired connections. That is, a computer may be in communication only with the patch 306, and the patch 306 may act as a receiver for data from patches 308a and 308b, which it may then transmit to the computer. The patch 306 can serve as a fixed, absolute reference for the patches 308a and 308b. For example, because the patch 306 is always in the same location on the fixed portion of the handle, it is possible to determine where patches 308a and 308b are with respect to the patch 306 (and, by extension, where patches 308a and 308b are with respect to each other). In some embodiments, the patches 308a and 308b can communicate with the computer via the patch 306. In some embodiments, the patches 308a and 308b can be communicate directly with the computer, for example, via a wired or wireless connection.

In some embodiments, raw data can be sent to a computer for further processing. In some embodiments, the sensor element 102 can perform some processing tasks, for example noise filtering, determining position or pose relative to other sensor packages, and so forth.

In some embodiments, motion of the patch 306 can be accounted for when determining the motion of the patches 308*a* and 308*b*. For example, if the entire handle rotates, such rotation can be subtracted the any rotation detected by the patches 308*a* and 308*b*. Similarly, if the handle is translated, such translation can be accounted for when determining the motion of the patches 308*a* and 308*b*. In some embodiments, multiple references patches can be used. For example, the use of multiple patches can enable determination of a point about which the handle has been rotated, enabling improved determination of the motion of the patches 308*a* and 308*b*.

In some embodiments, a graphical user interface may be implemented on a computer system. In some embodiments, the graphical user interface may be used to visualize orientation data received from the sensors. For example, a graphical user interface may be configured to display a model of a medical device and may provide various information about the positioning of the device and/or components thereof. For example, an interface may show a degree of rotation of a rotatable portion of a device handle. FIG. 4 depicts an example user interface according to some embodiments. In FIG. 4, a user interface 400 can have a display area 402 that shows a model of the device handle. The user interface 400 can include an overlay 404 that can display the rotation of the rotatable portions of the device handle with respect to a reference point 406. In some embodiments, the reference point may be the location of a fixed sensor on the device handle (for example, the patch 306 in FIG. 3). In some embodiments, the reference point may be another location on the device handle. For example, some device handles may have markers or other indicators that can be used as reference points. In some embodiments, a reference point may not be on the handle but can be another reference point, such as a point on a surgical table, wall, ceiling, floor, etc. In some embodiments, a user can manipulate the graphical user interface, for example to rotate the handle. In some embodiments, the graphical user interface can provide views from one or more fixed viewing directions, for example from multiple orthogonal planes. In some embodiments, a 3D model can be shown and can be freely manipulated by the user to enable viewing from arbitrary directions. It will be appreciated that FIG. 4 is merely exemplary. A similar interface with similar or the same functionality can be implemented for any type of surgical device handle or other means of manipulating a surgical device.

In some embodiments, a graphical user interface can show the position of a sensor inside a patient's body. For example, in some embodiments, a 2D and/or 3D model of the patient's body can be shown, and the location, orientation, pose, and so forth of the sensor can be shown. In some embodiments, a user can manipulate the graphical user interface, for example to observe pose, position, and so forth from different viewpoints.

FIG. 5 shows an example 3D model of a handle for a device according to some embodiments. As shown in FIG. 5, the handle may have a plurality of fixed and moveable sensors to enable tracking of the movements of the various movable parts of the handle, such as knobs, levers, and so forth.

In some embodiments, the visualization data may be presented in real time or in substantially real time. The sensor data may also be stored by a computer system for later review, learning, and other tasks as described herein.

In addition to orientation information, the sensor data may also be used to determine positioning with respect to a reference. In some embodiments, an electrostatic sensor may offer high sensitivity and may be relatively low cost. In some embodiments, an electrostatic sensor may be based on electrostatic induction or charge transfer. Electrostatic sensors may be available from vendors such as STMicroelectronics of Geneva, Switzerland. In some embodiments, an electrostatic sensor (for example, the sensor element 102 that includes an electrostatic sensor 210) may be inserted into a sheath that is equipped with one or more electrodes arranged along the length of the sheath, and the electrostatic sensor may measure electric potential variation as the electrostatic sensor moves along the sheath. By measuring the electric potential continuously and/or periodically, the electrostatic sensor data can be used to determine when the electrostatic sensor is nearby an electrode in the sheath and the trajectory of the electrostatic sensor (and thereby, the device to which it is attached) can be mapped. In some embodiments, an external camera or other system can be used to monitor how far the sheath has been inserted into a vessel of the patient and the location of electrodes in the sheath, and thus can be used to provide an additional reference point. In some embodiments, a user of a system may manually input an indication of how far the sheath has been inserted. For example, in some embodiments, a sheath can include fiducials that can be used to determine an insertion depth of the sheath. In some embodiments, an external camera system can be used to determine an initial position of the sheath, which can enable the determination of insertion depth. Advantageously, using a sheath with electrodes arranged along the length of the sheath does not require the use of external stimulators, for example, that may be placed on the skin. External stimulators present a variety of difficulties. For example, they may shift or fall off during a procedure, and signals may be weaker due to the greater distance as compared with electrodes that are embedded in or on a sheath and thus are in close proximity to an electrostatic sensor, intervening tissue, intervening fluids, and so forth.

FIG. 6A depicts an example embodiment of a sheath that can be used in combination with an electrostatic sensor for position detection according to some embodiments. A sheath 600 has a plurality of electrodes 602 that are spaced a known distance d apart. In some embodiments, the distance between adjacent electrodes may be constant, although this need not be so. For example, the spacing between electrodes 602 in a bulk region of the sheath may be greater than near an end of the sheath, or some other configuration may be used to achieve a desired sensitivity and positional resolution. A distal end of a catheter 605 may have an electrostatic sensor 607 (which may, for example, be the electrostatic sensor 210 of the sensor element 102) affixed to it (e.g., mounted inside the catheter, for example using a patch 100). The catheter 605 can be inserted into the sheath 600. The position of the catheter 605 may be determined by monitoring the change in signal from the electrostatic sensor 607 as it passes by the electrodes 602. In some embodiments, the sheath electrodes may be connected to an external stimulator that can stimulate the electrodes with an electronic signal, which may be sensed by the electrostatic sensor 607. For example, the electrodes 602 can be connected to a voltage source. In some embodiments, each electrode of the electrodes 602 can be connected to the same source. In some embodiments, different electrodes of the electrodes 602 can be connected to different sources, for example so that different electrodes are at different potentials.

In some embodiments, the orientation information and positional information from various sensors may be combined. For example, tracking information obtained from an electrostatic sensor may be improved or corrected by using information from an accelerometer and/or gyroscope. In some embodiments, data from sensors on the handle of a device (e.g., as shown in FIG. 3) may be combined with data from a sensor attached to a distal end of a device, for example as shown in FIG. 6A. Thus, a surgeon or other user may be able to visualize how movements and manipulations of the handle of the device (and any moveable components of the device handle) relate to movements of the distal end. For example, pushing forward on the handle of the device may result in a forward movement of the distal end, but they may not move by the same amount, for example due to kinking. Similarly, a rotation performed on the device handle may not translate perfectly into a rotation at the distal end, for example due to twisting along the shaft of a catheter.

While FIG. 6A illustrates a sheath with one or more electrodes embodied therein, a sheath can include additional or alternative features. For example, in some embodiments, a sheath can include one or more sensor elements such as an accelerometer, gyroscope, or magnetometer. For example, a sheath can include one or more MEMS devices. In some embodiments, multiple sensors can be included in the sheath. In some embodiments, the sensors can be, for example, MEMS devices that can include one or more sensors (e.g., one or more of an accelerometer, a gyroscope, a magnetometer, or an electrostatic sensor) in a single integrated circuit package. In some embodiments, the sheath can include wiring for providing power, signaling, or both for the sheath sensors.

FIG. 6B illustrates another sheath according to some embodiments. As shown in FIG. 6B, in some embodiments, the sheath 600 can have sensor elements 608 disposed along the length of the sheath 600. In some embodiments, the sensor elements 608 can be spaced in an equidistant manner, although this is not necessary. As described above with reference to FIG. 6A, it can be advantageous to have unequal spacing, such as closer spacing near the distal end of the sheath or any other arrangement that enables sufficient data collection. The sensor elements 608 can be similar to or the same as the sensor element 102.

Adaptable Sensor Capsule

While external sensors that attach to the handle of a surgical device as described herein may be readily adapted to many different existing surgical devices, sensors that are inserted into the body are commonly built into the surgical device. This can present many limitations. For example, many surgical devices may lack sensors at all, may not have the sensors a surgeon would like to use for a particular procedure, or may have sensors disposed in non-ideal locations (e.g., too far from the distal end). Thus, there is a need for a sensor package that can be used with existing surgical instruments. According to some embodiments herein, an adaptable sensor capsule can be fitted to a variety of existing surgical instruments to enable tracking, mapping, and other sensing applications. Advantageously, an adaptable sensor can be used with existing devices, thereby avoiding a need to purchase new devices, which surgeons and other medical staff may be unfamiliar with and which can have significant costs. As another advantage, a surgeon or other medical staff member can select a sensor based on the needs of the procedure, while still using familiar equipment.

For example, an adaptable sensor capsule can include pressure sensors, force sensors, temperature sensors, accelerometers, gyroscopes, magnetometers, electrostatic sensors, pH sensors, and so forth. The sensor capsule can be used in a wide array of medical settings. For example, a sensor capsule equipped with a pressure sensor can be used to monitor cardiovascular, respiratory, and/or intra-compartmental pressure. A sensor capsule with a pH sensor may be used to monitor the pH in the esophagus, for example to test for acid reflux or gastroesophageal reflux disease. Temperature sensors may be used to monitor core temperature in critically ill patients. In some embodiments, accelerometers, gyroscopes, magnetometers, and electrostatic sensors can be used to aid in the navigation of steerable medical device components during procedures such as mitral valve suturing, heart valve replacement, aneurysm surgery, neurosurgery, arthroscopy to diagnose or repair joint tissue, intrauterine fetal surgery, and so forth. The sensor capsules described herein can be used in a wide range of minimally invasive procedures. In some embodiments, the uses for such sensors can be limited only by the ability to make a sensor that small enough to operate in a desired area.

Sensors (e.g., sensor packages or sensor elements) can advantageously be attached on any kind of medical device. In some embodiments, sensors can be placed on or in any part of the device that enables convenient data acquisition. Sensor packages or sensor elements can be applied to medical devices to aid in several tasks. For example, sensor packages or sensor elements can be used to aid in the positioning of another medical device, for example when implanting a valve replacement, for use in the mapping phase of a procedure, when performing a minimally invasive joint replacement procedure, and so forth. Sensors may be removed from the body once the procedure is complete.

A flexible and customizable sensor capsule can be fitted to a wide variety of medical devices. The sensor capsule can be made in various sizes and shapes to fit medical devices with different sizes and shapes. Preferably, the sensor capsule can accommodate a range of shapes and sizes so sensor capsules do not have to be customized for each different medical device that could benefit from the use of a sensor capsule. For example, sensor capsules may be made in a few sizes that can fit a wide array of medical devices.

In some embodiments, the sensor capsule can be affixed around an exterior surface of a medical device. Advantageously, the sensor capsule can include sensors, a power source (e.g., a battery), and a communications module (e.g., a Bluetooth module, Bluetooth Low Energy (BLE) module, WiFi module, or other wireless communications module), although not all of these components may be present in some embodiments. The components can be mounted on a flexible substrate such as a polyimide film (e.g., Kapton) or other suitable flexible substrate to form a cylindrical or approximately cylindrical sensor capsule. In some embodiments, the substrate may comprise a biocompatible material. In some embodiments, the ends of the flexible substrate may be joined with an elastic material so that the sensor capsule can be tightly fitted to a range of medical devices with different diameters. For example, the sensor capsule can have a diameter of from about 2 mm to about 10 mm, or even larger if desired. For example, a larger capsule may be used in procedures with lesser space constraints, such as joint replacement, colonoscopy procedures, other gastroenterology procedures, and so forth. In some embodiments, an elastic material may not be used and another closure mechanism can be used, such as adjustable fasteners. In some embodiments, the substrate may be affixed to a shaft of the medical device using an adhesive. In some embodiments, the substrate may be held in place by a flexible wrap placed over the substrate and capsule components. In some embodiments, one or more materials may be biocompatible materials. In some embodiments, a sensor capsule may be flexible over a limited range, for example over a fixed range of diameters. In some embodiments, different sensor capsules can be provided to accommodate different diameter ranges. In some embodiments, rather than being flexible or adjustable, a sensor capsule can have a defined, static diameter, and different capsules can be provided with different fixed, static diameters.

In some embodiments, a flexible substrate may not be used. For example, in an alternative embodiment, a number of segments of a rigid substrate material (for example, two segments, three segments, four segments, five segments, six segments, seven segments, or more) can be electrically connected and arranged in a manner to fit around a medical device. In some embodiments, each segment can be connected to the other segments, either directly or indirectly. In some embodiments, not all segments may be electrically connected, directly or indirectly, to all other segments.

In some embodiments, the sensor capsule can be reusable, although in other embodiments the sensor capsule may be used for a single procedure. For example, the sensor capsule can include a non-rechargeable battery that lasts for a few hours (e.g., about the length of a single procedure), and the module can be discarded after the procedure. In some embodiments, a reusable sensor capsule can include inductive charging circuitry, thereby avoiding the use of ports, pins, and so forth that may complicate sterilization procedures. Similarly, a reusable implementation of the patch 100 described above can use inductive charging to charge a power source (e.g., battery) inside the patch 100. In a reusable sensor capsule or patch, components that make up the sensor capsule or patch can be chosen to be sterilizable (e.g., materials that can withstand an autoclave procedure or other cleaning).

Components may be relatively small in size. For example, batteries, communications modules, and sensors may be relatively thin (e.g., less than about 1 mm) and have lengths and widths of about 3 mm or less. Small, thin components can enable the sensor capsule to fit into tight spaces. In some embodiments, components may be longer along an axial direction (e.g., along the length of a catheter). In some embodiments, while the substrate is flexible, the components mounted to the substrate may not be flexible, which can present challenges to ensure that electrical and physical connections are maintained as the circuit is flexed. In some embodiments, flexible wiring can be used to ensure electrical connectivity is maintained as the flexible substrate is manipulated.

FIG. 7 shows an example illustration of a sensor capsule according to some embodiments. According to FIG. 7, a sensor capsule includes a flexible substrate 700. A communications module 702, sensor 704, and power source 706 are mounted to the flexible substrate 700. The sensor capsule is fitted to a medical device, such as at or near the distal end of a catheter.

FIG. 8 shows an end view of a medical device with a sensor capsule affixed thereto. In FIG. 8, the flexible substrate 700 is wrapped around a portion of the medical device. The communications module 702, sensor 704, and power source 706 are attached to the flexible substrate 800. The sensor capsule is wrapped in a flexible, waterproof wrap 802 to protect the components of the sensor capsule during the procedure. The wrap 802 also covers any sharp or pointy edges of the components of the sensor capsule, which could cause injury to a patient if left unprotected.

In some embodiments, the flexible substrate and the waterproof wrap may be thin, for example about 1 mm or less. The substrate may have a diameter of about 4 mm or less, while the flexible wrap may have a diameter of about 5 mm or less. In some embodiments, a rigid sleeve may be fitted over the sensor capsule electronic components, and the diameter of the waterproof wrap may be governed by the outer diameter of the sleeve. In other embodiments, a sleeve may not be used and the diameter of the wrap can be governed by the protrusion of the battery, communications module, and/or sensor from the substrate.

FIGS. 9A and 9B illustrate a sensor capsule with a flexible wrap placed on a shaft near the distal end according to some embodiments. As shown in FIGS. 9A and 9B, the flexible wrap may enclose the sensor capsule, and the sensor capsule (and associated wrap) may be about the same diameter or smaller than a payload (e.g., a replacement heart valve).

In the embodiments described above, the sensor capsule is shown at or near the distal end of a catheter. However, the sensor capsule may be deployed in many different ways. For example, sensor capsules can be placed at any desirable location along a catheter shaft or other surgical device component that is inserted into the patient. In some embodiments, a sensor capsule can be relatively large and can, for example, be fitted to a handle of a surgical instrument.

In some cases, it may be preferable to dispose the components of the sensor capsule along the axis rather than around the axis. Such a design can be useful in many circumstances, such as when it is necessary or advantageous to minimize the diameter of the sensor capsule, for example when performing a procedure that requires the sensor to be in or pass through narrower openings, for example narrow blood vessels. FIG. 10 illustrates a sensor capsule with axially-distributed components according to some embodiments. A flexible substrate 1000 has components 1002, 1004, and 1006 disposed along its axis. The components can include batteries, sensors, and/or communications modules. While a structure such as that in FIG. 10 can reduce the diameter of the sensor capsule, the added length can impact flexibility and maneuvering of the shaft. Other arrangements may be used in some embodiments. For example, some components may be disposed along the axis while others are disposed around the axis. The arrangement around and along the axis can be selected to achieve a desired combination of diameter and flexibility.

In some embodiments, a sensor capsule may include additional components or fewer components. For example, some embodiments may include two or more sensor devices instead of one. Some embodiments can include a memory module for capturing data. Some embodiments may not have a communications module (for example, a user could retrieve information captured by the sensors after the procedure is complete).

FIGS. 11A-11D show example embodiments of a sensor module having components distributed on a substrate. As shown in FIGS. 11A-11D, in some embodiments, the substrate 1100 may be sub-divided into one or more flat portions and/or may include one or more curved portions.

FIGS. 12A-12C show example embodiments of a sensor module having components distributed about a substrate. As in FIGS. 11A-11D, the embodiments of FIGS. 12A-12C can have substrates that can be segmented into one or more flat portions and/or one or more curved portions. In some embodiments, portions can overlap. For example, FIGS. 12A and 12C show a curved portion of a sensor module overlaid on top of a flag portion, although other configurations are possible.

Orientation Tracking

During some medical procedures, orientation information can be important. For example, when performing a transcatheter aortic valve replacement (TAVR) procedure, it can be important to properly align the replacement valve with the commissures of the patient's own valve. For example, as shown in FIG. 13, an aortic valve 1300 can have commissures 1302. Preferably, the features of a replacement valve can be aligned with the commissures 1302. While surgical intervention can still be effective even with some degree of commissural misalignment, such misalignment can make future interventions more difficult. Thus, proper alignment can be especially important for younger patients who may need future medical interventions that may be more difficult if the replacement valve is not properly aligned.

In a conventional procedure, a physician may rely on CT scans of the patient and radiomarkers that can be identified using fluoroscopy during a procedure. In some embodiments, an external marker near the handle of a catheter device can help the physician to orient the valve. However, while these methods can help to avoid severe or moderate misalignment (e.g., a misalignment of about 30 degrees or more), some degree of misalignment may still be observed as measuring the orientation of the valve is still somewhat crude. For example, due to twisting, kinking, and so forth, an external marker may not accurately reflect the true orientation of the valve. In some embodiments, CT scans may be performed prior to a surgical procedure and thus there can be some error due to differing positioning of the patient as well as a lack of real-time information about the patient's anatomy. In some embodiments, real time two-dimensional x-ray data can be available to aid the surgeon in placing the implant (e.g., as captured using a fluoroscope), but two-dimensional representations provide limited information and proper placement of the implant can still be difficult. Some embodiments described herein may be used to improve misalignment. For example, some embodiments herein may be used to reduce misalignment to up to about 25 degrees, up to about 20 degrees, up to about 15 degrees, up to about 10 degrees, up to about 5 degrees, or up to about 1 degree, for example from about 5 degrees to about 25 degrees, about 5 degrees to about 15 degrees, or about 10 degrees to about 15 degrees, depending upon the specific implementation, the skill of the surgeon, and so forth.

In some embodiments, a sensor element can be included at the tip of a catheter. The replacement valve can be fixed to the catheter so that the valve and catheter move together. Thus, if a rotation of the sensor element on the catheter is known, the rotation of the replacement valve can also be known. In some embodiments, the sensor element can include a gyroscope that can be used to determine the rotation of the catheter (and thereby, the replacement valve), which can aid in orienting the valve inside the patient.

In some embodiments, the sensor element may be part of an adaptable sensor capsule as described above. In other embodiments, the sensor element may be permanently built into the catheter, into a delivery system, or any other component. In some embodiments, a sensor element can additionally or alternatively be built into the replacement valve.

In some embodiments, the positioning of the sensor package can be calibrated based on CT scans of the patient. In some embodiments, another sensor, emitter, beacon, or similar device can act as a reference point for the sensor package, as discussed in more detail below. In some embodiments, both a reference and CT scans can be used in combination.

In some embodiments, additional sensor elements may be disposed along the length of the catheter and may be used in conjunction with a sensor element (e.g., in a sensor capsule) at or near the distal end of the catheter to provide additional information for tracking the orientation of the replacement valve. In some embodiments, a sensor element can be used to detect and account for movements due to respiration and/or heartbeats, as described herein.

In some cases, respiration and/or heartbeats can alter the positioning of a sensor package, delivery system, replacement valve, and so forth inside the patient. Accordingly, in some embodiments, a system can be configured to process positional and/or motion data (e.g., velocity, acceleration, rotation) to account for movements caused by respiration, heartbeats, shifting of the patient during a procedure, and so forth. In some embodiments, one or more reference points (e.g., sensors, emitters, beacons, and/or the like) can be placed on the skin of the patient, for example on the patient's chest, to capture respiratory and/or heartbeat movements, although this approach may be less accurate than using reference points located inside the patient near where a procedure is to take place. For example, a motion sensor placed on the patient's skin may not fully capture the motion of the patient's heart due to intervening bone, soft tissue, fluids, and so forth.

In some embodiments, a reference sensor can advantageously be placed inside the patient in a known location. For example, a pigtail or other device (e.g., a catheter) can be inserted into the patient and placed near the location where a procedure is to be performed. If a movement is detected by both the reference sensor and a sensor on another instrument (e.g., a sensor located at or near the distal end of a catheter or sheath), the movement can, in some embodiments, be attributed to external motion sources such as heartbeats, breathing, or movement of the patient during the procedure, rather than resulting from, for example, an intentional rotation, translation, and so forth of the instrument. In some embodiments, the motion of the reference sensor can be subtracted from the motion of a sensor on another instrument.

FIG. 14A illustrates an example of the use a reference sensor according to some embodiments. The example of FIG. 14A illustrates use in, for example, a TAVR procedure. A reference sensor element 1402 can be affixed to a pigtail 1404. The pigtail 1404 can extend out of the patient, for example from the patient's heart and out through the patient's leg. In some embodiments, the pigtail 1404 can have an outlet port disposed at or near the distal end of the pigtail 1404. The outlet port can be used to flow a contrast agent into the patient's body near the site of the procedure. For example, a contrast agent can be flowed into the patient through the outlet port when the pigtail 1404 is close to the location where the procedure is being performed. For example, in the case of a heart valve replacement procedure, contrast can be flowed in when the distal end of the pigtail 1404 is within the heart. Surgical staff can use medical imaging methods such as fluoroscopy to visualize the contrast and the position of the distal end of the pigtail 1404, thereby enabling the surgical staff to have a visual representation that can be used to confirm the placement of the distal end of the pigtail 1404 (and thereby, the location of the reference sensor element 1402). In some embodiments, surgeons or other surgical staff can make use of 3D, patient-specific aorta anatomy determined from CT scans. The pigtail 1404 can be positioned in a lowest point of a cusp (e.g., left coronary cusp, right coronary cusp, or non-coronary cusp) and can act as a reference point for a sensor element 1408 disposed in or on a catheter 1410. In some embodiments, the catheter 1410 can have an implant 1412 (e.g., a replacement valve) affixed at or near the distal end of the catheter 1410. The location of the sensor element 1408 can be determined (e.g., by an external computer and/or by processing hardware on board the sensor element 1408 or the reference sensor element 1402 relative to the reference sensor element 1402. In some embodiments, any motion of the reference sensor element 1402 can be attributed to effects such as the patient's heart beating, the patient breathing, the patient shifting during a surgical procedure, and so forth. The motion of the reference sensor element 1402 can be subtracted from the motion of the sensor element 1408, enabling determination of the position of the sensor element 1408 relative to the valve plane 1414.

In some embodiments, a system can be configured to provide a graphical representation (e.g., a 3D graphical representation) that shows the location of the replacement valve relative to the patient's anatomy. For example, a graphical interface can provide a depiction similar to the one shown in FIG. 14A. The graphical interface can provide a real-time, or nearly real-time, representation that accurately represents the location of the replacement valve within the patient.

FIG. 14B illustrates the relative positioning of the reference sensor element 1402 and sensor element 1408 at various points in a TAVR procedure, for example as the replacement valve is being inserted into place. With the aid of the reference sensor element 1402, the position of the sensor element 1408 (and thus, the position of the replacement valve) above the valve plane 1414 can be known. Similarly, the relative position of the sensor element 1408 and reference sensor element 1402 can be used to determine a location and/or orientation of the TAVR axis 1416.

FIG. 15 depicts an example embodiment of a catheter device 1500. The device 1500 can have a handle 1502. The handle 1502 can be equipped with one or more controls for manipulating a catheter shaft and/or the distal end thereof. In some embodiments, the handle 1502 and/or the controls thereon can be fitted with one or more sensors as described herein. In some embodiments, the device 1500 can include a shaft 1504 and an end piece 1506. The end piece may be used to contain and/or deploy an implant, for example an implant as may be used in a TAVR procedure. The end piece 1506 can be fitted with a sensor package 1508. The sensor package 1508 can include one or more accelerometers, gyroscopes, and so forth to enable the detection of translation and/or rotation of the end piece 1506. The data from the sensor package 1508 can be used, in some embodiments, to aid in commissural alignment during a TAVR procedure.

In some embodiments, there can be one or more sensor elements 1510 disposed along the length of the shaft 1504. The one or more sensor elements 1510 may, for example, be used to aid in more accurately determining the position of the end piece 1506. In some embodiments, the one or more sensor elements 1510 can be used to detect potential issues during a procedure. For example, if the different sensors packages or sensor elements detect inconsistent amounts of rotation and/or translation, such inconsistency may indicate that there is a kink in the shaft 1504, that the shaft 1504 is twisting, that the shaft 1504 is stuck due to an obstruction, and so forth. Such deformations or obstructions can potentially be hazardous as they may result in collapse of the shaft 1504, sudden untwisting of the shaft 1504, sudden movement of the shaft 1504, and so forth. Thus, it can be important for a surgeon to know when such a condition may be occurring so that the surgeon can take appropriate remedial measures.

In some embodiments, the sensor package 1508 and one or more sensor elements 1510 can be wireless. For example, the sensor package 1508 and one or more sensor elements 1510 may be battery-powered and may communicate sensor information wirelessly, for example via Bluetooth or another communication method as described herein. In some embodiments, the sensor package 1508 and one or more sensor elements 1510 can be wired. For example, the sensor package 1508 and one or more sensor elements 1510 can receive power via wired connections and/or can send signals over a wired connection to an outside receiver (for example, a computer or other hardware for interfacing with the sensor package 1508 and one or more sensor elements 1510). In some embodiments, at least one of the sensor package 1508 and the one or more sensor elements 1510 can be can be battery powered and communicate wirelessly and at least one of the sensor package 1508 and the one or more sensor elements 1510 can be wired.

As discussed briefly above, catheter positions are often monitored using fluoroscopy. While fluoroscopy provides limited data, it may still be valuable to capture this data. In some embodiments, a user may select a precise region of interest (for example, a position on a catheter), and artificial intelligence/computer vision software may be used to track the region of interest during a procedure. This may enable a better understanding of the correlation between movements of a device handle and movements of the device inside the body. The fluoroscopy tracking data could be used as an alternative to having a sensor package or sensor element embedded in the distal end of a catheter) or in addition to using a sensor package. For example, for some devices or procedures, it may not be practical to include a sensor that can go inside the body. In some embodiments, a combination of sensor packages (e.g., capsules and/or patches) can be used in conjunction with other tracking techniques.

Hand and Finger Tracking

In addition to tracking movement of medical instruments, it may also be valuable to track the movements of a surgeon's hand and/or the hands of any other surgical staff that are manipulating instruments or the patient. FIG. 16 depicts an example glove according to some embodiments which may be used to track hand and finger movements. The glove 1600 has a plurality of finger sensors 1602 (which may comprise the sensor element 102 or a different sensor element). In some embodiments, each finger may have more than one sensor, for example three sensors, so that fine motion of the fingers can be tracked. The glove 1600 may have a reference sensor 1604 (which may comprise the sensor element 102 or a different sensor package). In some embodiments, the finger sensors 1602 may communicate with the reference sensor via a wired connection, although some implementations may use wireless communications (for example, to prevent wires from interfering with the movements of the surgeon). In some embodiments, the reference sensor 1604 may be connected to an external data receiver such as a computer and may transmit data to the receiver, for example via a wired or wireless connection.

Data Platform

Sensor data. fluoroscopy data, camera video captures, and so forth may be used in real time (for example, for real time visualizations or alerts). Such data may, additionally or alternatively, be stored for subsequent review, machine learning, and so forth. Thus, in some embodiments, data may be directed by a system to various destinations, for example to a computer in an operating suite for real-time visualization and to a data store for later use. In some embodiments, the sensors, cameras, fluoroscopes, and so forth may be in communication with a collector unit that can collect the sensor data and send it to appropriate destinations. The collector unit may be, for example, a hardware device that receives sensor data and interfaces with a computer to make the data available for visualization, storage, and other uses.

In some embodiments, the collector may have built-in functionality that allows it to route data to appropriate destinations without the aid of an external device such as a computer. For example, the collector may include a built-in WiFi or ethernet connection and may be configured with software that enables it to transfer data across a network or other connection. In some embodiments, the collector may receive data in a standardized log format and may transmit the data as soon as it is received to a real-time message system server. In some embodiments, the collector can be configured to cache data for sending at a later time and/or may temporarily store a copy of the data. In some embodiments, a processor application may be used to save and store the information. In some embodiments, the collector may receive data in different formats and may convert the data to one or more standardized formats. For example, the collector may convert capacitance values, resistance values, or other electrical signals into acceleration and orientation data, may standardize data into particular units, may standardize time and date stamps, may convert videos and images to standard formats, and so forth. In some embodiments, the collector may receive and/or transmit data using an application programming interface (API). In some embodiments, the collector may be implemented using a single board computer such as a Raspberry Pi, available from the Raspberry Pi Foundation of Cambridge, England. As discussed above, in some embodiments, circuitry that is part of a sensor package can be configured to perform some processing tasks before the data is transmitted to an external device such as a collector or other computing device.

In some embodiments, sensor data may be combined with other data about the patient, for example demographic information about the patient, information about the patient's health history, medical test results, and so forth. In some embodiments, information from multiple healthcare facilities may be combined into a single data lake or each facility may maintain its own data lake. In some embodiments, information may be shared between data lakes and/or multiple healthcare facilities may have access to a single data lake that contains information from more than one healthcare facility.

Because the data may be used to review individual procedures, to develop predictive models that may impact patient care, and so forth, data integrity can be important. In some embodiments, the data may be stored in an immutable format. In some embodiments, data may be stored in a time series database (TSDB). A TSDB may offer several advantages over conventional relational databases. For example, time-series data often has fewer relationships between data points in different tables, and the relative simplicity and uniformity of the data can allow for significant performance improvements over relational databases. However, TSDBs are often configured to decay (for example, by reducing the precision of numerical values) and/or delete data on a set schedule, which may not be desirable. For example, older data may be useful for model training, for litigation defense, and so forth.

In some embodiments, a ledger database may be used to store sensor data. Ledger databases track transactions that modify, add, or delete database entries, leaving an auditable trail. This may be especially advantageous in scenarios where data integrity is a major concern, for example in malpractice litigation when it may be useful to review the movements that were performed during a surgical procedure. While a ledger database offers advantages such as tracking modifications, a ledger database may be slower and may require more computing resources. Thus, while a TSDB is often computationally light enough to be run locally, a ledger database may be run on an external system such as a server, which may add complexity and potential failure points (for example, data may not be stored if a network connection becomes unavailable).

In some embodiments, multiple types of databases may be used to store data. For example, a TSDB may be deployed on a local computing device in the operating room (or elsewhere on the healthcare facility's network) to enable rapid capture of sensor data, and the data may be transferred to a ledger database for long term storage, model training, and so forth. In some embodiments, a TSDB may be deployed and used remotely.

Various approaches may be used to ensure that patient data is stored securely and in a manner that complies with applicable regulations. For example, in some embodiments, data may be encrypted on the client (e.g., healthcare facility) side prior to being uploaded to a cloud server. In some embodiments, only the client may have the encryption key or keys to decrypt the data. In some embodiments, a database may log all activity to facilitate review by a client, and access to information may be based on role. In some embodiments, patient data may be anonymized prior to storage. For example, patients may be identified by a randomly generated patient ID, which may be assigned by the cloud server. In some embodiments, the randomly generated patient ID may change over time. In some embodiments, patient health information and personal identifying information may be anonymized, for example by using k-anonymity algorithms. In some embodiments, data may be shared among healthcare facilities in a secure and/or anonymized manner. In some embodiments, organizations may share some information, such as models trained using patient data, but may not share actual patient data.

The data platform may be used in a variety of ways. One application is to aid surgeons and healthcare staff in reviewing medical procedures. For example, a surgeon may be able to log in to a platform and review procedures they have performed, including visualizing their hand movements, device handle movements, and catheter tip movements, as well as any other motion that was monitored during the procedure. A surgeon may be able to review fluoroscope images and any other data or images that were collected during the procedure. Surgeons may use this information to develop better procedures. In some embodiments, some users may be able to review procedures for multiple surgeons, for example all surgeons within a healthcare organization. This kind of review may be used to compare surgeons, to determine possible efficiency gains, and so forth.

Predictive Engine

Many use cases for surgical movement data involve descriptive analytics such as, for example, reviewing movements during a procedure, aggregating data to understand efficiencies, outcomes, and so forth. In some embodiments, the captured movement data can be used in a predictive analytics engine that can be used to predict patient outcomes.

In some embodiments, different healthcare organizations may connect to a common platform and choose to share data with one or more other healthcare organizations to form a data collaborative. Healthcare organizations may then perform queries against this larger dataset, without necessarily being given access to the underlying data. For example, organizations may compute statistics for the overall data collaborative, or may compare organizations within the data collaborative. For example, organizations may look at number of procedures, overall statistics about the patients, average procedure duration, average procedure cost, average outcomes for different types of patients, and so forth.

In some embodiments, members of the data collaborative may have access to a machine learning framework that can use all the data from the data collaborative as training data for an AI model to predict patient outcomes given movements during surgery and other health parameters such as patient age, gender, weight, laboratory data, health conditions, and so forth.

FIG. 17 depicts an example block diagram of a process that may be run on a computing system for training an AI/ML model according to some embodiments. At block 1701, the system may receive a dataset that includes, for example, movement information, patient health information, and so forth. At block 1702, one or more transformations may be performed on the data. In some embodiments, data from a collector as described above may already be standardized and may undergo relatively minor transformations such as data normalization steps to prepare the data for training. In some cases, however, more significant transformations may be carried out on the data. For example, data received from electronic medical record platforms and so forth, which may vary from healthcare organization to healthcare organization, may require extensive transformations. For example, different healthcare organizations may use different electronic medical record systems, may store data in different formats, and so forth. Thus, in some embodiments, the system may convert the data into standardized formats suitable for training. At block 1703, the system may create, from the received dataset, training, tuning, and testing/validation datasets. The training dataset 1704 may be used during training to determine variables for forming a predictive model. The tuning dataset 1705 may be used to select final models and to prevent or limit overfitting that may occur during training with the training dataset 1704, as the trained model should be generally applicable, rather than tuned to the particularities of the training dataset 1704. The testing dataset 1706 may be used after training and tuning to evaluate the model. For example, the testing dataset 1706 may be used to check if the model is overfitted to the training dataset. The system, in training loop 1714, may train the model at 1707 using the training dataset 1704. Training may be conducted in a supervised, unsupervised, or partially supervised manner. At 1708, the system may evaluate the model according to one or more evaluation criteria. For example, the evaluation may include a measure of how often the model correctly predicts patient outcomes, how often the model recommends movements that would likely be successful, how often the model recommends movements that would likely fail, how often the model incorrectly predicts positive outcomes, and so forth. At 1709, the system may determine if the model meets the one or more evaluation criteria. If the model fails evaluation, the system may, at 1710, tune the model using the tuning dataset 1705, repeating the training 1707 and evaluation 1708 until the model passes the evaluation at 1709. Once the model passes the evaluation at 1709, the system may exit the model training loop 1714. The testing dataset 1706 may be run through the trained model 1711 and, at block 1712, the system may evaluate the results. If the evaluation fails, at block 1713, the system may reenter training loop 1714 for additional training and tuning. If the model passes, the system may stop the training process, resulting in a trained model 1711.

After the AI model is trained, users within the data collaborative may be able to upload information about a specific patient and may receive from the trained AI system a recommendation for movements to be executed during a procedure and/or other information such as the likelihood of a positive outcome for the patient. In some embodiments, a system may convert the received patient information into a standardized format for use by the trained AI model. In some embodiments, an optimized procedural movement guide may be available to a surgeon during the procedure. In some embodiments, a system may alert the surgeon if their movements deviate from the recommended procedure. In some embodiments, deviating from the recommended procedure may trigger additional data collection, such as data collection from additional sources and/or increased data collection rates.

Computer Systems

FIG. 18 is a block diagram depicting an embodiment of a computer hardware system configured to run software for implementing one or more embodiments of the systems, methods, and devices disclosed herein.

In some embodiments, the systems, processes, and methods described herein are implemented using a computing system, such as the one illustrated in FIG. 18. The example computer system 1802 is in communication with one or more computing systems 1820, portable devices 1815, and/or one or more data sources 1822 via one or more networks 1818. While FIG. 18 illustrates an embodiment of a computing system 1802, it is recognized that the functionality provided for in the components and modules of computer system 1802 may be combined into fewer components and modules, or further separated into additional components and modules.

The computer system 1802 can comprise a module 1814 that carries out the functions, methods, acts, and/or processes described herein (e.g., processes as discussed above). The module 1814 is executed on the computer system 1802 by a central processing unit 1806 discussed further below.

In general, the word "module," as used herein, refers to logic embodied in hardware or firmware or to a collection of software instructions, having entry and exit points. Modules are written in a programming language, such as JAVA, C or C++, Python, or the like. Software modules may be compiled or linked into an executable program, installed in a dynamic link library, or may be written in an interpreted language such as BASIC, PERL, LUA, or Python. Software modules may be called from other modules or from themselves, and/or may be invoked in response to detected events or interruptions. Modules implemented in hardware include connected logic units such as gates and flip-flops, and/or may include programmable units, such as programmable gate arrays or processors.

Generally, the modules described herein refer to logical modules that may be combined with other modules or divided into sub-modules despite their physical organization or storage. The modules are executed by one or more computing systems and may be stored on or within any suitable computer readable medium or implemented in-whole or in-part within special designed hardware or firmware. Not all calculations, analysis, and/or optimization require the use of computer systems, though any of the above-described methods, calculations, processes, or analyses may be facilitated through the use of computers. Further, in some embodiments, process blocks described herein may be altered, rearranged, combined, and/or omitted.

The computer system 1802 includes one or more processing units (CPU) 1806, which may comprise a microprocessor. The computer system 1802 further includes a physical memory 1810, such as random-access memory (RAM) for temporary storage of information, a read only memory (ROM) for permanent storage of information, and a mass storage device 1804, such as a backing store, hard drive, rotating magnetic disks, solid state disks (SSD), flash memory, phase-change memory (PCM), 3D XPoint memory, diskette, or optical media storage device. Alternatively, the mass storage device may be implemented in an array of servers. Typically, the components of the computer system 1802 are connected to the computer using a standards-based bus system. The bus system can be implemented using various protocols, such as Peripheral Component Interconnect (PCI), Micro Channel, SCSI, Industrial Standard Architecture (ISA) and Extended ISA (EISA) architectures.

The computer system 1802 includes one or more input/output (I/O) devices and interfaces 1812, such as a keyboard, mouse, touch pad, and printer. The I/O devices and interfaces 1812 can include one or more display devices, such as a monitor, that allows the visual presentation of data to a user. More particularly, a display device provides for the presentation of GUIs as application software data, and multi-media presentations, for example. The I/O devices and interfaces 1812 can also provide a communications interface to various external devices. The computer system 1802 may comprise one or more multi-media devices 1808, such as speakers, video cards, graphics accelerators, and microphones, for example.

The computer system 1802 may run on a variety of computing devices, such as a server, a Windows server, a Structure Query Language server, a Unix Server, a personal computer, a laptop computer, a Graphic Processing Unit, a digital signal processor, and so forth. In other embodiments, the computer system 1802 may run on a cluster computer system, a mainframe computer system and/or other computing system suitable for controlling and/or communicating with large databases, performing high volume transaction processing, and generating reports from large databases. The computing system 1802 is generally controlled and coordinated by an operating system software, such as z/OS, Windows, Linux, UNIX, BSD, SunOS, Solaris, macOS, iOS, iPadOS, Android, or other compatible operating systems, including proprietary operating systems. Operating systems control and schedule computer processes for execution, perform memory management, provide file system, networking, and I/O services, and provide a user interface, such as a graphical user interface (GUI), among other things.

The computer system 1802 illustrated in FIG. 18 is coupled to a network 1818, such as a LAN, WAN, or the Internet via a communication link 1816 (wired, wireless, or a combination thereof). Network 1818 communicates with various computing devices and/or other electronic devices. Network 1818 is communicating with one or more computing systems 1820, one or more portable devices 1815 and one or more data sources 1822. The module 1814 may access or may be accessed by computing systems 1820, portable devices 1815 and/or data sources 1822 through a web-enabled user access point. Connections may be a direct physical connection, a virtual connection, and other connection type. The web-enabled user access point may comprise a browser module that uses text, graphics, audio, video, and other media to present data and to allow interaction with data via the network 1818.

Access to the module 1814 of the computer system 1802 by computing systems 1820, portable devices 1815, and/or by data sources 1822 may be through a web-enabled user access point such as the computing systems' 1820 or data source's 1822 personal computer, cellular phone, smartphone, laptop, tablet computer, e-reader device, audio player, or another device capable of connecting to the network 1818. Such a device may have a browser module that is implemented as a module that uses text, graphics, audio, video, and other media to present data and to allow interaction with data via the network 1818.

The output module may be implemented as a combination of an all-points addressable display such as a cathode ray tube (CRT), a liquid crystal display (LCD), a plasma display, or other types and/or combinations of displays. The output module may be implemented to communicate with input devices 1812 and they also include software with the appropriate interfaces which allow a user to access data through the use of stylized screen elements, such as menus, windows, dialogue boxes, tool bars, and controls (for example, radio buttons, check boxes, sliding scales, and so forth). Furthermore, the output module may communicate with a set of input and output devices to receive signals from the user.

The input device(s) may comprise a keyboard, roller ball, pen and stylus, mouse, trackball, voice recognition system, or pre-designated switches or buttons. The output device(s) may comprise a speaker, a display screen, a printer, or a voice synthesizer. In addition, a touch screen may act as a hybrid input/output device. In another embodiment, a user may interact with the system more directly such as through a system terminal connected to the score generator without communications over the Internet, a WAN, or LAN, or similar network.

In some embodiments, the system 1802 may comprise a physical or logical connection established between a remote microprocessor and a mainframe host computer or a cluster for the express purpose of uploading, downloading, or viewing interactive data and databases on-line in real time. The remote microprocessor may be operated by an entity operating the computer system 1802, including the client server systems or the main server system, and/or may be operated by one or more of the data sources 1822, one or more of the portable devices 1815 and/or one or more of the computing systems 1820. In some embodiments, terminal emulation software may be used on the microprocessor for participating in the micro-mainframe link.

In some embodiments, computing systems 1820 who are internal to an entity operating the computer system 1802 may access the module 1814 internally as an application or process run by the CPU 1806.

In some embodiments, one or more features of the systems, methods, and devices described herein can utilize a URL and/or cookies, for example for storing and/or transmitting data or user information. A Uniform Resource Locator (URL) can include a web address and/or a reference to a web resource that is stored on a database and/or a server. The URL can specify the location of the resource on a computer and/or a computer network. The URL can include a mechanism to retrieve the network resource. The source of the network resource can receive a URL, identify the location of the web resource, and transmit the web resource back to the requestor. A URL can be converted to an IP address, and a Domain Name System (DNS) can look up the URL and its corresponding IP address. URLs can be references to web pages, file transfers, emails, database accesses, and other applications. The URLs can include a sequence of characters that identify a path, domain name, a file extension, a host name, a query, a fragment, scheme, a protocol identifier, a port number, a username, a password, a flag, an object, a resource name and/or the like. The systems disclosed herein can generate, receive, transmit, apply, parse, serialize, render, and/or perform an action on a URL.

A cookie, also referred to as an HTTP cookie, a web cookie, an internet cookie, and a browser cookie, can include data sent from a website and/or stored on a user's computer. This data can be stored by a user's web browser while the user is browsing. The cookies can include useful information for websites to remember prior browsing information, such as a shopping cart on an online store, clicking of buttons, login information, and/or records of web pages or network resources visited in the past. Cookies can also include information that the user enters, such as names, addresses, passwords, credit card information, etc. Cookies can also perform computer functions. For example, authentication cookies can be used by applications (for example, a web browser) to identify whether the user is already logged in (for example, to a web site). The cookie data can be encrypted to provide security for the consumer. Tracking cookies can be used to compile historical browsing histories of individuals. Systems disclosed herein can generate and use cookies to access data of an individual. Systems can also generate and use JSON web tokens to store authenticity information, HTTP authentication as authentication protocols, IP addresses to track session or identity information, URLs, and the like.

The computing system 1802 may include one or more internal and/or external data sources (for example, data sources 1822). In some embodiments, one or more of the data repositories and the data sources described above may be implemented using a relational database, such as DB2, Sybase, Oracle, CodeBase, and Microsoft® SQL Server as well as other types of databases such as a flat-file database, an entity relationship database, and object-oriented database, and/or a record-based database.

The computer system 1802 may also access one or more databases 1822. The databases 1822 may be stored in a database or data repository. The computer system 1802 may access the one or more databases 1822 through a network 1818 or may directly access the database or data repository through I/O devices and interfaces 1812. The data repository storing the one or more databases 1822 may reside within the computer system 1802.

ADDITIONAL EMBODIMENTS

In the foregoing specification, the invention has been described with reference to specific embodiments thereof. It will, however, be evident that various modifications and changes may be made thereto without departing from the broader spirit and scope of the invention. The specification and drawings are, accordingly, to be regarded in an illustrative rather than restrictive sense.

Indeed, although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

It will be appreciated that the systems and methods of the disclosure each have several innovative aspects, no single one of which is solely responsible or required for the desirable attributes disclosed herein. The various features and processes described above may be used independently of one another or may be combined in various ways. All possible combinations and subcombinations are intended to fall within the scope of this disclosure.

Certain features that are described in this specification in the context of separate embodiments also may be implemented in combination in a single embodiment. Conversely, various features that are described in the context of a single embodiment also may be implemented in multiple embodiments separately or in any suitable subcombination. Moreover, although features may be described above as acting in certain combinations and even initially claimed as such, one or more features from a claimed combination may in some cases be excised from the combination, and the claimed combination may be directed to a subcombination or variation of a subcombination. No single feature or group of features is necessary or indispensable to each and every embodiment.

It will also be appreciated that conditional language used herein, such as, among others, "can," "could," "might," "may," "e.g.," and the like, unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous and are used inclusively, in an open-ended fashion, and do not exclude additional elements, features, acts, operations, and so forth. In addition, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise. Similarly, while operations may be depicted in the drawings in a particular order, it is to be recognized that such operations need not be performed in the particular order shown or in sequential order, or that all illustrated operations be performed, to achieve desirable results. Further, the drawings may schematically depict one or more example processes in the form of a flowchart. However, other operations that are not depicted may be incorporated in the example methods and processes that are schematically illustrated. For example, one or more additional operations may be performed before, after, simultaneously, or between any of the illustrated operations. Additionally, the operations may be rearranged or reordered in other embodiments. In certain circumstances, multitasking and parallel processing may be advantageous. Moreover, the separation of various system components in the embodiments described above should not be understood as requiring such separation in all embodiments, and it should be understood that the described program components and systems may generally be integrated together in a single software product or packaged into multiple software products. Additionally, other embodiments are within the scope of the following claims. In some cases, the actions recited in the claims may be performed in a different order and still achieve desirable results.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 4.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present. The headings provided herein, if any, are for convenience only and do not necessarily affect the scope or meaning of the devices and methods disclosed herein.

Accordingly, the claims are not intended to be limited to the embodiments shown herein, but are to be accorded the widest scope consistent with this disclosure, the principles and the novel features disclosed herein.

What is claimed is:

1. A system for monitoring motion during a medical procedure, the system comprising:

a first catheter configured for insertion into a patient, the catheter comprising:

an end piece configured to deploy an implant, and a first sensor element positioned on the end piece, the first sensor element configured to provide information about a position of the first sensor element and translational and/or angular displacement of the first sensor element relative to a reference location within the patient;

a second catheter configured for insertion into a patient, the second catheter comprising a second sensor element positioned at a distal end of the second catheter, the second sensor element configured to provide information about a position of the second sensor element and translational and/or angular displacement of the second sensor element relative to the reference location, and the second catheter configured to position the second sensor element at the reference location; and a computer-readable medium and a processor, wherein the processor is configured to execute instructions stored in the computer-readable medium to cause the processor to:

determine a relative position between the first sensor element and the second sensor element to determine a position of the end piece relative to the reference location; and subtract the translational and/or angular displacement of the second sensor element from the translational and/or angular displacement of the first sensor element to account for movement of the patient.

2. The system of claim 1, wherein the medical procedure is a transcatheter aortic valve replacement (TAVR) procedure, and the implant comprises a replacement valve.

3. The system of claim 2, wherein the second catheter comprises a pigtail catheter.

4. The system of claim 3, wherein the pigtail catheter comprises an outlet port disposed near the distal end thereof, the outlet port configured to enable delivery of a contrast agent into the patient.

5. The system of claim 3, wherein the reference location is a lowest point left coronary cusp, a right coronary cusp, or a non-coronary cusp.

6. The system of claim 5, wherein the processor determines the relative position between the first sensor element and the second sensor element to indicate a position of the implant relative to a valve plane.

7. The system of claim 1, wherein the first catheter comprises a steerable catheter.

8. The system of claim 7, wherein the first catheter comprises:

a handle including one or more user inputs, a catheter shaft, and the end piece positioned on a distal end of the catheter shaft.

9. The system of claim 8, wherein the first sensor element is configured to determine a rotational position of the end piece.

10. The system of claim 8, wherein the catheter shaft comprises one or more catheter shaft sensor elements disposed along a length of the catheter shaft.

11. The system of claim 10, wherein the processor is configured to determine that the catheter shaft has kinked based on one or more outputs of the one or more catheter shaft sensor elements.

12. The system of claim 10, wherein the processor is configured to determine that the catheter shaft has twisted based on one or more outputs of the one or more catheter shaft sensor elements.

13. The system of claim 1, wherein the processor causes display, on a graphical user interface, of the relative position of the first sensor element and the second sensor element.

14. The system of claim 1, wherein the first sensor element is positioned on a patch that is adhesively attached to the end piece.

15. The system of claim 1, wherein the first sensor element is positioned in or on a sensor capsule, the sensor capsule further comprising a flexible wrap comprising a biocompatible material, wherein the flexible wrap is configured to secure the sensor capsule to the end piece.

\* \* \* \* \*